United States Patent
Borate et al.

(10) Patent No.: US 8,324,227 B2
(45) Date of Patent: Dec. 4, 2012

(54) THIENO[2,3-D]-PYRIMIDIN-4(3H)-ONE COMPOUNDS WITH ANTIFUNGAL PROPERTIES AND PROCESS THEREOF

(75) Inventors: Hanumant Bapurao Borate, Pune (IN); Suleman Riyajsaheb Maujan, Pune (IN); Sangmesher Prabhakar Sawargave, Pune (IN); Sheerang Vidhyadhar Joshi, Mumbai (IN); Sharangi Vaiude, Mumbai (IN); Mohan Anand Chandavarkar, Mumbai (IN)

(73) Assignee: FDC Limited, Mumbai, IN (US)

( * ) Notice: Subject to any disclaimer, the term of this patent is extended or adjusted under 35 U.S.C. 154(b) by 339 days.

(21) Appl. No.: 12/742,211

(22) PCT Filed: Sep. 5, 2008

(86) PCT No.: PCT/IN2008/000571
§ 371 (c)(1),
(2), (4) Date: May 10, 2010

(87) PCT Pub. No.: WO2009/109983
PCT Pub. Date: Sep. 11, 2009

(65) Prior Publication Data
US 2010/0273815 A1    Oct. 28, 2010

(30) Foreign Application Priority Data

Mar. 3, 2008  (IN) ............................ 438/MUM/2008

(51) Int. Cl.
C07D 495/04  (2006.01)
A61K 31/519  (2006.01)
A01N 43/54   (2006.01)

(52) U.S. Cl. .................... 514/267; 514/260.1; 544/278; 544/250

(58) Field of Classification Search .................. 544/278, 544/250; 514/260.1, 267
See application file for complete search history.

(56) References Cited

FOREIGN PATENT DOCUMENTS

| | | |
|---|---|---|
| EP | 1282084 | 2/2003 |
| IN | 1424/MUM/2005 | 8/2007 |
| WO | 97/05130 | 2/1997 |

OTHER PUBLICATIONS

Goodman et al. (N. Engl. J. Med., 1992, 326, pp. 845-851, abstract).*
Lebouvier et al., Synthesis and antifungal activities of new fluconazole analogues with azaheterocycle moiety, Bioorg Med Chem Lett. Jul. 1, 2007;17(13):3686-9.

* cited by examiner

*Primary Examiner* — Susanna Moore
(74) *Attorney, Agent, or Firm* — Kramer & Amado, P.C.

(57) ABSTRACT

The present invention discloses novel compounds of the Formula (1), containing thieno-[2,3-d]pyrimidin-4(3H)-one moieties and pharmaceutically acceptable salts thereof, methods for preparing these compounds, the use of these compounds in prevention and treatment of fungal infections, and pharmaceutical preparations containing these novel compounds.

11 Claims, No Drawings

THIENO[2,3-D]-PYRIMIDIN-4(3*H*)-ONE COMPOUNDS WITH ANTIFUNGAL PROPERTIES AND PROCESS THEREOF

TECHNICAL FIELD

The present invention relates to novel compounds of the Formula (1), containing thieno-[2,3-d]pyrimidin-4(3H)-ones moieties and pharmaceutically acceptable salts thereof, methods for preparing these compounds, the use of these compounds in prevention and treatment of fungal infections, and to pharmaceutical preparations containing these novel compounds.

BACKGROUND AND PRIOR ART

Fungal infections are the major problem in the treatment of immuno-compromised patients and those suffering from AIDS. The current antifungal agents belong to various groups like polyenes, allylamines, antimetabolites, azoles, glucan synthesis inhibitors etc. Fluconazole is a member of the family of azole antifungals. Fluconazole is orally active and has low toxicity but its extensive use has resulted in emergence of fluconazole-resistant fungal strains. Therefore, it is necessary to meet the long-felt need to develop novel fluconazole analogues which exert high anti-fungal activity against various fungi including *Candida albicans, Aspergillus niger* and *Fusarium proliferatum* with MIC values 2 to 8 fold lower than that of fluconazole.

The presence of one triazole ring, halogenated phenyl ring and tertiary alcoholic oxygen functionality in fluconazole is necessary for activity. The present invention seeks to provide novel azoles and process thereof as an effort to come up with antifungal agents with broad spectrum of antifungal activity. Fluconazole analogues have been reported having antifungal activity in the literature.

A series of fluconazole analogues incorporating azaindole and indole moieties were described in "Synthesis and antifungal activities of new fluconazole analogues with azoheterocycle moiety", Bioorg Med Chem Lett 2007 Jul. 1; 17(13), 3686-9.

OBJECTS OF THE INVENTION

The primary objective of the present invention is to provide compounds of Formula (1), containing thieno-[2,3-d]pyrimidin-4(3H)-one moieties with high anti-fungal activity against various fungi including *C. albicans, Aspergillus. niger* and *F. proliferatum* and the process for the preparation of said antifungal compounds.

SUMMARY OF THE INVENTION

Accordingly, to meet the above stated objective, the present invention discloses novel fluconazole analogues of Formula (1) containing thieno-[2,3-d]pyrimidin-4(3H)-one moieties, which are useful as antifungal compounds with MIC values 2 to 8 fold lower than that of fluconazole.

In one aspect, the invention provides novel compounds of formula (1), wherein, R1 is hydrogen or halogen selected from fluorine, chlorine, bromine or iodine;

R2 is hydrogen or halogen selected from fluorine, chlorine, bromine and iodine; and R3 and R4 which may be the same or different and each represents a hydrogen, alkyl group of linear or branched chain of 1 to 20 carbon atoms optionally substituted with aryl group, hydroxyl group, alkanoate group, acetoxy group, amino acetyloxy group, N-Boc-amino acetyloxy group, alkoxy(—OR) group (wherein R=alkyl group with 1 to 4 carbon atoms), benzyloxy, arylalkyl group (wherein the aryl group is phenyl which is either unsubstituted or substituted with alkyl group of 1 to 3 carbon atoms) or cycloalkyl group with 3 to 10 carbon atoms.

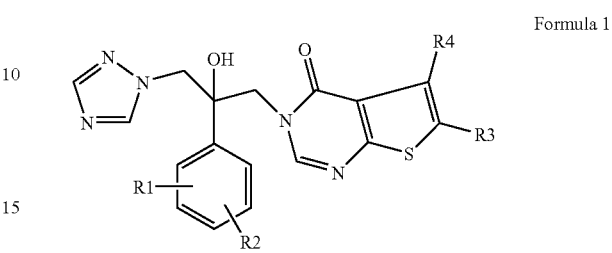

Formula 1

In another aspect, the invention provides a process for the preparation of the compounds of Formula (1) using various synthetic methods. Accordingly, the present invention describes a general process for the preparation of compounds of the Formula (1) wherein R1, R2, R3 and R4 are as defined above, which comprises reacting substituted 2-aminothiophene-3-carboxylates of the Formula (3) with formamide and ammonium acetate to collect the thienopyrimidinones of the Formula (4), followed by reacting the compounds of the Formula (4) with epoxide of the Formula (5) in presence of a suitable base to obtain the compounds of the Formula 1.

The said suitable base may be selected from various organic or inorganic bases well described in the art.

In yet another aspect, the invention discloses a pharmaceutical preparation which comprises a compound of formula (1) in association with at least one pharmaceutical excipient.

DETAILED DESCRIPTION

The invention will now be described in detail in connection with certain preferred and optional embodiments, so that various aspects thereof may be more fully understood and appreciated.

According to the present invention, there are provided novel antifungal compounds of Formula (1). These compounds are analogues of fluconazole that are active against fungi and used in pharmaceutical preparations as active agents.

In a preferred embodiment, there are provided the novel compounds of Formula 1,

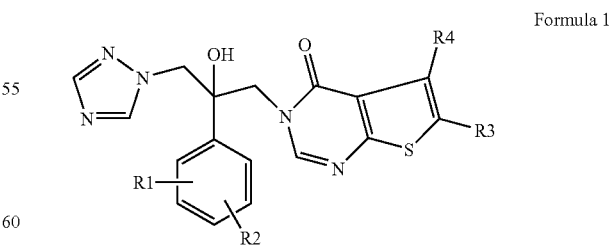

Formula 1 wherein,
R1 is hydrogen, halogen selected from fluorine, chlorine, bromine or iodine;
R2 is hydrogen, halogen selected from fluorine, chlorine, bromine or iodine, R3 and R4 which may the same or different and each represents a hydrogen, alkyl group of linear or branched chain of 1 to 20 carbon atoms optionally substituted with aryl group, hydroxyl group, alkanoate group, acetoxy group, amino acetyloxy group, N-Boc-amino acetyloxy group, alkoxy(—OR) group (wherein R=alkyl group with 1 to 4 carbon atoms), benzyloxy, arylalkyl group (wherein the aryl group is phenyl which is either unsubstituted or substituted with alkyl group of 1 to 3 carbon atoms) or cycloalkyl group with 3 to 10 carbon atoms.

The present invention encompasses all the novel compounds and their stereochemically isomeric forms or their pharmaceutically acceptable salts.

In another preferred embodiment, the invention describes process for preparation of the compounds of formula (1). The compounds of the present invention may be prepared by adapting the route depicted in Scheme 1. As depicted in Scheme 1, the compounds of Formula (3) are converted to the compounds of Formula (4), wherein R3 and R4 are as defined above. In a further step, the compounds of Formula (4) are converted to the compounds of Formula (1) by reacting with the compounds of Formula (5), wherein R1 is hydrogen or a halogen selected from fluorine, chlorine, bromine and iodine; R2 is hydrogen or a halogen selected from fluorine, chlorine, bromine and iodine.

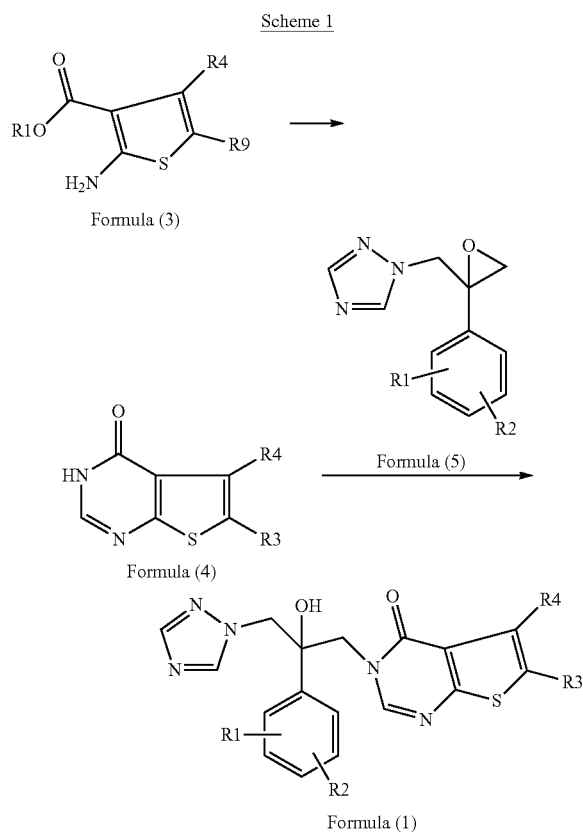

Scheme 1

Accordingly, the general process for the preparation of compounds of Formula 1, comprises steps of
a) preparing 2-amino-4 and/or 5-substituted thiophene-3-carboxylate of formula (3), wherein R1 is methyl or ethyl; and R3 and R4 are as defined above by Gewald synthesis;

b) contacting 2-amino-4 and/or 5-substituted thiophene-3-carboxylate of Formula (3) with formamide and ammonium acetate to obtain the thieno-[2,3-d]-pyrimidin-4(3H)-one of Formula (4), wherein R3 and R4 are as defined above, and c) treating the compound of Formula (4) with epoxide of Formula (5), wherein R1 and R2 are as defined above, in presence of a base to obtain the compound of Formula (1).

The said suitable base may be selected from various organic or inorganic bases well described in the art.

In another preferred embodiment, the invention discloses a pharmaceutical preparation which comprises a compound of formula (1) in association with at least one pharmaceutical excipient known in art.

The invention further provides a method for treating or preventing a fungal infection in a subject, which comprises administering an effective amount of the compound of formula (1) in association with pharmaceutical excipients.

The compounds of formula (1) can be conveniently administered to a patient in oral unit dosage form and prepared by any of the methods well-known in the pharmaceutical arts.

Dosage forms include solid dosage forms like tablets, powders, capsules, sachets, troches and lozenges as well as liquid syrups, suspensions and elixirs. The active ingredient(s) and excipients can be formulated into compositions and dosage forms according to methods known in the art.

Accordingly, the compounds of formula (1) or their pharmaceutically acceptable salt can be milled into a powder and be used in a pharmaceutical product/composition or physically modified such as by granulation to produce larger granules. The compounds of formula (1) or their pharmaceutically acceptable salt can also be used to prepare a liquid pharmaceutical composition by dissolving or dispersing or suspending/emulsifying it in a pharmaceutically acceptable liquid medium such as water, glycerin, vegetable oil and the like as discussed in greater detail below.

When a dosage form such as a tablet is made by compaction of a powdered composition, the composition is subjected to pressure from a punch and dye. Solid and liquid compositions can also be dyed using any pharmaceutically acceptable colorant to improve their appearance and/or to facilitate patient identification of the product and unit dosage level.

In liquid pharmaceutical compositions of the present invention, the compounds of formula (1) or their pharmaceutically acceptable salt and any other solid excipients are dissolved or suspended in a liquid carrier such as water, vegetable oil, alcohol, polyethylene glycol, propylene glycol or glycerin. Liquid pharmaceutical compositions can contain emulsifying agents to disperse an active ingredient or other excipient that is not soluble in the liquid carrier uniformly throughout the composition.

Selection of particular excipients and the amounts to use can be readily determined by the formulation scientist based upon experience and consideration of standard procedures and reference works in the field. The solid compositions of the present invention include powders, granulates, aggregates and compacted compositions.

The compounds of formula (1) or their pharmaceutical salt can also be used to prepare topical preparations such as shampoos, lotions, gels, foams, creams, transdermal patches and greasy ointments.

Still in another object, the use of the compounds of formula (1) for the preparation of medicament useful for the treatment or prevention of fungal infections is provided by the invention.

The invention is further illustrated with the following examples and should not be construed to limit the scope of the present invention. The features of the present invention will become more apparent from the following description of the inventive concept and the description of the preferred embodiments and appended claims.

Example 1

General Synthetic Procedure for Preparation of Compounds of the Formula 1

Procedure A:
Thienopyrimidinones of the Formula (4) (1 mmol), epoxide of formula (5) (1 mmol) and sodium methoxide (1.2 mmol) were taken in 2-neck RB flask under inert atmosphere, dry t-butanol (5-10 ml) was added to the above reaction mixture and the mixture was stirred under reflux for 10 to 30 hrs. Upon completion of the reaction, t-butanol was removed on rotavapor, water was added to the reaction mixture, the compound from the reaction mixture was extracted with ethyl acetate, dried and concentrated. Purification by column chromatography afforded the pure compounds of the Formula (1).

Procedure B:
Thienopyrimidinone of the Formula (4) (1 mmol) and epoxide of formula (5) (1 mmol) were taken in 2-neck RB flask under inert atmosphere, dry ethyl acetate (10-15 ml) was added followed by flame dried potassium carbonate (2 mmol) and tetrabutylammonium bromide (1.2 mmol). The mixture was stirred under reflux for 2 to 10 hrs, cooled, diluted with water, extracted with ethyl acetate, dried and concentrated. Purification by column chromatography afforded the pure compounds of the Formula (1).

Some functional group transformations like debenzylation, deacetylation, protection of hydroxyl functionality etc provided more number of compounds. The following novel compounds of formula (1) were prepared by using the above synthetic methods (see Table 1).

Example 2

6-(3-Benzyloxypropyl)-3-[2-(2,4-difluorophenyl)-2-hydroxy-3-[1,2,4]-triazol-1-ylpropyl]-thieno[2,3-d]pyrimidin-4(3H)-one (1-A02)

6-(3-Benzyloxypropyl)-thieno[2,3-d]pyrimidin-4(3H)-one of Formula (4-A02) (3.0 g, 0.01 mole), 1[[2-(2,4-difluorophenyl)oxiranyl]methyl]-1H-1,2,4-triazole of the Formula (5) (2.82 g, 0.012 mole) and sodium methoxide (0.65 g, 0.012 mole), were taken in two neck round bottom flask under inert atmosphere, dry t-butanol (70 ml) was added to the above reaction mixture and the mixture was stirred under reflux for 12 hours. t-Butanol was removed on rotavapor, water (50 ml) was added to the reaction mixture, the compound from the reaction mixture was extracted with ethyl acetate (3×50 ml), dried, concentrated and purified by column chromatography to obtain the pure 6-(3-benzyloxypropyl)-3-[2-(2,4-difluorophenyl)-2-hydroxy-3-[1,2,4]triazol-1-ylpropyl]-thieno[2,3-d]pyrimidin-4(3H)-one (1-A02) (0.8 gm, 14%). 1HNMR (CDCl3, 200 MHz):: 1.91-2.06 (m, 2H), 2.95 (t, J=6 Hz, 2H), 3.51 (t, J=6 Hz, 2H), 4.21 (d, J=14 Hz, 1H), 4.49 (s, 2H), 4.52 (d, J=14 Hz, 1H), 4.72 (d, J=14 Hz, 1H), 4.79 (d, J=14 Hz, 1H), 6.22 (s, 1H), 6.72-6.88 (m, 2H), 7.08 (s, 1H), 7.31 (bs, 5H), 7.49-7.62 (m, 1H), 7.83 (s, 1H), 7.91 (s, 1H), 8.09 (s, 1H).

Example 3

3-[2-(2,4-Difluorophenyl)-2-hydroxy-3-[1,2,4]-triazol-1-yl-propyl]-5,6,7,8-tetrahydrobenzothieno[2,3-d]pyrimidin-4(3H)-one (1-A09)

5,6,7,8-Tetrahydrobenzothieno[2,3-d]pyrimidin-4(3H)-one of Formula (4-A09) (1.0 g, 4.8 mmole), 1[[2-(2,4-difluorophenyl)oxiranyl]methyl]-1H-1,2,4-triazole of the Formula (5) (1.38 g, 5.8 mmole) and sodium methoxide (0.31 g, 5.8 mmole), were taken in two neck round bottom flask under inert atmosphere, dry t-butanol (30 ml) was added to the above reaction mixture and the mixture was stirred under reflux for 12 hours. t-Butanol was removed on rotavapor, water (20 ml) was added to the reaction mixture, the compound from the reaction mixture was extracted with ethyl acetate (3×20 ml), dried, concentrated and purified by column chromatography to obtain the pure 3-[2-(2,4-Difluorophenyl)-2-hydroxy-3-[1,2,4]triazol-1-yl-propyl]-5,6,7,8-tetrahydrobenzothieno[2,3-d]pyrimidin-4(3H)-one (1-A09) (1.29 gm, 60%). 1HNMR (CDCl3, 200 MHz): 1.74-1.96 (m, 4H), 2.71-2.81 (m, 2H), 2.90-3.02 (m, 2H), 4.18 (d, J=14 Hz, 1H), 4.55 (d, J=14 Hz, 1H), 4.70 (d, J=14 Hz, 1H), 4.77 (d, J=14 Hz, 1H), 6.29 (bs, 1H), 6.72-6.92 (m, 2H), 7.51-7.62 (m, 1H), 7.85 (s, 2H), 8.13 (s, 1H).

Example 4

3-[2-(2,4-Difluorophenyl)-2-hydroxy-3-[1,2,4]-triazol-1-yl-propyl]-6-(3-acetoxypropyl)-thieno[2,3-d]pyrimidin-4(3H)-one (1-A26)

6-(3-Acetoxypropyl)-thieno[2,3-d]pyrimidin-4(3H)-one of Formula (4-A26) (0.5 g, 2 mmole) and 1[[2-(2,4-difluorophenyl)oxiranyl]methyl]-1H-1,2,4-triazole of the Formula (5) (0.47 g, 2 mmole) were taken in two neck round bottom flask under inert atmosphere, dry ethyl acetate (5 ml) was added followed by flame dried potassium carbonate (0.55 g, 4 mmole) and tetrabutylammonium bromide (0.76 g, 2.4 mmole) the mixture was stirred under reflux for 12 hours, Cooled, diluted with water (15 ml), extracted with ethyl acetate (3×10 ml), dried, concentrated and purified by column chromatography afforded the pure 3-[2-(2,4-difluorophenyl)-2-hydroxy-3-[1,2,4]triazol-1-yl-propyl]-6-(3-acetoxypropyl)-thieno[2,3-d]pyrimidin-4(3H)-one (1-A26) (0.3 gm, 31%). 1HNMR (CDCl3, 200 MHz): 1.96-2.10 (m, 2H), 2.06 (s, 3H), 2.92 (t, J=8 Hz, 2H), 4.11 (t, J=6 Hz, 2H), 4.27 (d, J=14 Hz, 1H), 4.60 (d, J=14 Hz, 1H), 4.73 (d, J=14 Hz, 1H), 4.85 (d, J=14 Hz, 1H), 6.74-6.92 (m, 2H), 7.10 (s, 1H), 7.45-7.59 (m, 1H), 7.91 (bs, 1H), 7.95 (s, 1H), 8.36 (bs, 1H).

Following compounds were prepared by following either of the general procedures described above.

5) 6-(4-Benzyloxybutyl)-3-[2-(2,4-difluorophenyl)-2-hydroxy-3-[1,2,4]triazol-1-ylpropyl]-thieno[2,3-d]pyrimidin-4(3H)-one (1-A01)

This compound was prepared by procedure B using 6-(4-benzyloxybutyl)-thieno[2,3-d]pyrimidin-4(3H)-one and 1[[2-(2,4-difluorophenyl)oxiranyl]methyl]-1H-1,2,4-triazole of the Formula (5). 1HNMR (CDCl3, 200 MHz): 1.61-1.86 (m, 4H), 2.84 (t, J=6 Hz, 2H), 3.49 (t, J=6 Hz, 2H), 4.23 (d, J=16 Hz, 1H), 4.49 (s, 2H), 4.53 (d, J=16 Hz, 1H), 4.72 (d, J=16 Hz, 1H), 4.80 (d, J=16 Hz, 1H), 6.22 (s, 1H), 6.72-6.90 (m, 2H), 7.08 (s, 1H), 7.32 (bs, 5H), 7.50-7.62 (m, 1H), 7.84 (s, 1H), 7.92 (s, 1H), 8.10 (s, 1H).

6) 3-[2-(2,4-Difluorophenyl)-2-hydroxy-3-[1,2,4]-triazol-1-yl-propyl]-6-(n-hexyl)-thieno[2,3-d]pyrimidin-4(3H)-one (1-A03)

1HNMR (CDcl3, 200 MHz):: 0.88 (t, J=6 Hz, 3H), 1.21-1.48 (m, 6H), 1.61-1.76 (m, 2H), 2.82 (t, J=8 Hz, 2H), 4.22 (d, J=15 Hz, 1H), 4.52 (d, J=15 Hz, 1H), 4.72 (d, J=15 Hz, 1H), 4.80 (d, J=15 Hz, 1H), 6.24 (s, 1H), 6.75-6.89 (m, 2H), 7.07 (s, 1H), 7.48-7.62 (m, 1H), 7.83 (s, 1H), 7.91 (s, 1H), 8.10 (s, 1H).

7) 3-[2-(2,4-Difluorophenyl)-2-hydroxy-3-[1,2,4]-triazol-1-yl-propyl]-6-n-pentylthieno[2,3-d]pyrimidin-4(3H)-one (1-A04)

1HNMR ($CDCl_3$, 200 MHz):: 0.90 (t, J=6 Hz, 3H), 1.27-1.42 (m, 4H), 1.64-1.76 (m, 2H), 2.82 (t, J=8 Hz, 2H), 4.21 (d, J=15 Hz, 1H), 4.52 (d, J=15 Hz, 1H), 4.71 (d, J=15 Hz, 1H), 4.78 (d, J=15 Hz, 1H), 6.24 (s, 1H), 6.76-6.88 (m, 2H), 7.06 (s, 1H), 7.50-7.64 (m, 1H), 7.81 (s, 1H), 7.90 (s, 1H), 8.09 (s, 1H).

8) 5-n-Butyl-3-[2-(2,4-difluorophenyl)-2-hydroxy-3-[1,2,4]-triazol-1-yl-propyl]-6-n-propyl-thieno[2,3-d]pyrimidin-4(3H)-one (1-A05)

1HNMR (CDcl3, 200 MHz):: 0.93 (t, J=6 Hz, 3H), 0.99 (t, J=6 Hz, 3H), 1.30-1.48 (m, 2H), 1.58-1.76 (m, 4H), 2.73 (t, J=6 Hz, 2H), 2.78-2.96 (m, 2H), 4.29 (d, J=14 Hz, 1H), 4.59 (d, J=14 Hz, 1H), 4.64 (d, J=14 Hz, 1H), 4.76 (d, J=14 Hz, 1H), 6.40 (bs, 1H), 6.72-6.89 (m, 2H), 7.48-7.60 (m, 1H), 7.86 (s, 2H), 8.18 (s, 1H).

9) 3-[2-(2,4-Difluorophenyl)-2-hydroxy-3-[1,2,4]-triazol-1-yl-propyl]-6-n-heptylthieno[2,3-d]pyrimidin-4(3H)-one (1-A06)

1HNMR (CDcl3, 200 MHz):: 0.86 (t, J=6 Hz, 3H), 1.21-1.32 (m, 8H), 1.62-1.72 (m, 2H), 2.81 (t, J=8 Hz, 2H), 4.23 (d, J=15 Hz, 1H), 4.53 (d, J=15 Hz, 1H), 4.72 (d, J=15 Hz, 1H), 4.80 (d, J=15 Hz, 1H), 6.24 (bs, 1H), 6.74-6.89 (m, 2H), 7.06 (s, 1H), 7.48-7.60 (m, 1H), 7.84 (s, 1H), 7.91 (s, 1H), 8.13 (s, 1H).

10) 3-[2-(2,4-Difluorophenyl)-2-hydroxy-3-[1,2,4]-triazol-1-yl-propyl]-3,5,6,7-tetrahydrocyclopenta[4,5]thieno[2,3-d]pyrimidin-4(3H)-one (1-A07)

1HNMR (CDcl3, 200 MHz): 2.39-2.55 (m, 2H), 2.95 (t, J=7 Hz, 2H), 3.02 (t, J=7 Hz, 2H), 4.18 (d, J=14 Hz, 1H), 4.55 (d, J=14 Hz, 1H), 4.73 (d, J=14 Hz, 1H), 4.80 (d, J=14 Hz, 1H), 6.26 (bs, 1H), 6.74-6.92 (m, 2H), 7.51-7.63 (m, 1H), 7.85 (s, 2H), 8.15 (s, 1H).

11) 3-[2-(2,4-Difluorophenyl)-2-hydroxy-3-[1,2,4]triazol-1-yl-propyl]-6-methyl-5-npentyl-thieno[2,3-d]pyrimidin-4(3H)-one (1-A08)

1HNMR (CDcl3, 200 MHz):: 0.89 (t, J=6 Hz, 3H), 1.22-1.50 (m, 6H), 2.39 (s, 3H), 2.71-2.93 (m, 2H), 4.27 (d, J=14 Hz, 1H), 4.58-4.81 (m, 6H), 6.41 (bs, 1H), 6.72-6.88 (m, 2H), 7.48-7.62 (m, 1H), 7.85 (bs, 2H), 8.18 (bs, 1H).

12) 3-[2-(2,4-Difluorophenyl)-2-hydroxy-3-[1,2,4]-triazol-1-yl-propyl]-6-n-hexyl-5-methyl-thieno[2,3-d]pyrimidin-4(3H)-one (1-A10)

1HNMR (CDcl3, 200 MHz):: 0.88 (t, J=6 Hz, 3H), 1.20-1.43 (m, 6H), 1.55-1.68 (m, 2H), 2.44 (s, 3H), 2.74 (t, J=8 Hz, 2H), 3.20 (bs, 1H), 4.22 (d, J=14 Hz, 1H), 4.59-4.88 (m, 6H), 6.74-6.92 (m, 2H), 7.48-7.62 (m, 1H), 7.89 (bs, 2H), 8.39 (bs, 1H).

13) 3-[2-(2,4-Difluorophenyl)-2-hydroxy-3-[1,2,4]triazol-1-yl-propyl]-5-methyl-6-npentyl-thieno[2,3-d]pyrimidin-4(3H)-one (1-A11)

1HNMR (CDcl3, 200 MHz):: 0.90 (bt, J=6 Hz, 3H), 1.30-1.45 (m, 4H), 1.56-1.69 (m, 2H), 2.43 (s, 3H), 2.74 (t, J=8 Hz, 2H), 4.24 (d, J=14 Hz, 1H), 4.66 (d, J=14 Hz, 1H), 4.74 (d, J=14 Hz, 1H), 4.86 (d, J=14 Hz, 1H), 6.72-6.92 (m, 2H), 7.46-7.59 (m, 1H), 7.92 (s, 1H), 7.95 (s, 1H), 8.55 (bs, 1H).

14) 6-(7-Acetoxyheptyl)-3-[2-(2,4-difluorophenyl)-2-hydroxy-3-[1,2,4]-triazol-1-ylpropyl]-thieno[2,3-d]pyrimidin-4(3H)-one (1-A12)

1HNMR (CDcl3, 200 MHz):: 1.21-1.36 (m, 6H), 1.51-1.80 (m, 4H), 2.03 (s, 3H), 2.81 (t, J=8 Hz, 2H), 4.03 (t, J=6 Hz, 2H), 4.25 (d, J=14 Hz, 1H), 4.56 (d, J=14 Hz, 1H), 4.72 (d, J=14 Hz, 1H), 4.82 (d, J=14 Hz, 1H), 6.72-6.88 (m, 2H), 7.06 (s, 1H), 7.47-7.61 (m, 1H), 7.87 (bs, 1H), 7.92 (s, 1H), 8.23 (bs, 1H).

15) 3-[2-(2,4-Difluorophenyl)-2-hydroxy-3-[1,2,4]triazol-1-yl-propyl]-6-(7-hydroxy heptyl)-thieno[2,3-d]pyrimidin-4(3H)-one (1-A13)

6-(7-Acetoxyheptyl)-3-[2-(2,4-difluorophenyl)-2-hydroxy-3-[1,2,4]triazol-1-ylpropyl]-thieno[2,3-d]pyrimidin-4(3H)-one (3.00 g, 5.5 mmol) was dissolved in the mixture of methanol (10 ml) and water (2 ml). Then potassium carbonate (760 mg, 5.5 mmol) was added and the mixture was stirred at RT for 2 hours. Methanol was then removed on rotavapor, water (10 ml) was added to the reaction mixture and extracted with ethyl acetate (2×5 ml), dried, concentrated and purified by column chromatography to obtain the pure 3-[2-(2,4-difluorophenyl)-2-hydroxy-3-[1,2,4]triazol-1-yl-propyl]-6-(7-hydroxyheptyl)-thieno[2,3-d]pyrimidin-4(3H)-one (2.5 gm, 90.57%).

$^1$HNMR ($CDCl_3$, 200 MHz): 1.25-1.42 (m, 6H), 1.49-1.80 (m, 4H), 2.81 (t, J=8 Hz, 2H), 3.62 (t, J=6 Hz, 2H), 4.25 (d, J=14 Hz, 1H), 4.57 (d, J=14 Hz, 1H), 4.72 (d, J=14 Hz, 1H), 4.82 (d, J=14 Hz, 1H), 6.27 (bs, 1H), 6.72-6.89 (m, 2H), 7.06 (s, 1H), 7.42-7.61 (m, 1H), 7.87 (bs, 1H), 7.92 (s, 1H), 8.25 (bs, 1H).

16) 3-[2-(2,4-Difluorophenyl)-2-hydroxy-3-[1,2,4]triazol-1-yl-propyl]-5(2-phenylethyl)-thieno[2,3-d]pyrimidin-4(3H)-one (1-A14)

1HNMR (CDCl3, 200 MHz):: 2.90 (t, J=8 Hz, 3H), 3.22 (t, J=8 Hz, 3H), 4.30 (d, J=14 Hz, 1H), 4.63 (d, J=14 Hz, 1H), 4.72 (d, J=14 Hz, 1H), 4.86 (d, J=14 Hz, 1H), 6.70-6.90 (m, 3H), 7.15-7.31 (m, 5H), 7.40-7.61 (m, 1H), 7.90 (bs, 1H), 7.99 (s, 1H), 8.33 (bs, 1H).

17) 6-Benzyl-3-[2-(2,4-difluorophenyl)-2-hydroxy-3-[1,2,4]-triazol-1-yl-propyl]-5-methyl-thieno[2,3-d]pyrimidin-4(3H)-one (1-A15)

1HNMR (CDcl3, 200 MHz):: 2.51 (s, 3H), 4.09 (s, 2H), 4.21 (d, J=14 Hz, 1H), 4.61 (d, J=14 Hz, 1H), 4.74 (d, J=14 Hz, 1H), 4.84 (d, J=14 Hz, 1H), 6.65-6.91 (m, 2H), 7.15-7.34 (m, 5H), 7.45-7.61 (m, 1H), 7.89 (s, 1H), 7.90 (s, 1H), 8.36 (bs, 1H).

18) 6-n-Decyl-3-[2-(2,4-difluorophenyl)-2-hydroxy-3-[1,2,4]triazol-1-yl-propyl]thieno[2,3-d]pyrimidin-4(3H)-one (1-A16)

1HNMR (CDCl3, 200 MHz):: 0.87 (t, J=6 Hz, 3H), 1.14-1.44 (m, 14H), 1.55-1.77 (m, 2H), 2.81 (t, J=8 Hz, 2H), 4.27 (d, J=14 Hz, 1H), 4.61 (d, J=14 Hz, 1H), 4.72 (d, J=14 Hz, 1H), 4.84 (d, J=14 Hz, 1H), 6.73-6.92 (m, 2H), 7.06 (s, 1H), 7.44-7.61 (m, 1H), 7.90 (bs, 1H), 7.93 (s, 1H), 8.35 (bs, 1H).

19) 3-[2-(2,4-Difluorophenyl)-2-hydroxy-3-[1,2,4]-triazol-1-yl-propyl]-6-n-nonylthieno[2,3-d]pyrimidin-4(3H)-one (1-A17)

1HNMR (CDCl3, 200 MHz):: 0.86 (t, J=6 Hz, 3H), 1.13-1.42 (m, 12H), 1.54-1.80 (m, 2H), 2.80 (t, J=8 Hz, 2H), 4.26 (d, J=14 Hz, 1H), 4.57 (d, J=14 Hz, 1H), 4.72 (d, J=14 Hz, 1H), 4.82 (d, J=14 Hz, 1H), 6.27 (bs, 1H), 6.73-6.92 (m, 2H), 7.06 (s, 1H), 7.44-7.61 (m, 1H), 7.87 (bs, 1H), 7.92 (s, 1H), 8.25 (bs, 1H).

20) 3-[2-(2,4-Difluorophenyl)-2-hydroxy-3-[1,2,4]-triazol-1-yl-propyl]-6-(n-propyl)-thieno[2,3-d]pyrimidin-4(3H)-one (1-A18)

1HNMR (CDCl3, 200 MHz):: 0.99 (t, J=7 Hz, 3H), 1.61-1.83 (m, 2H), 2.80 (t, J=8 Hz, 2H), 4.27 (d, J=14 Hz, 1H), 4.59 (d, J=14 Hz, 1H), 4.73 (d, J=14 Hz, 1H), 4.84 (d, J=14 Hz, 1H), 6.28 (bs, 1H), 6.74-6.90 (m, 2H), 7.08 (s, 1H), 7.46-7.61 (m, 1H), 7.88 (s, 1H), 7.92 (s, 1H), 8.28 (s, 1H).

21) 3-[2-(2,4-Difluorophenyl)-2-hydroxy-3-[1,2,4]-triazol-1-yl-propyl]3,5,6,7,8,9,10,11,12,13,14-undecahydrocyclododeca[4,5]thieno[2,3-d]pyrimidin-4(3H)-one (1-A19)

1HNMR (CDCl$_3$, 200 MHz):: 1.10-1.57 (m, 12H), 1.59-1.83 (m, 4H), 2.66-2.97 (m, 4H), 4.27 (d, J=14 Hz, 1H), 4.58 (d, J=14 Hz, 1H), 4.66 (d, J=14 Hz, 1H), 4.79 (d, J=14 Hz, 1H), 6.33 (bs, 1H), 6.72-6.90 (m, 2H), 7.46-7.90 (m, 1H), 7.86 (s, 1H), 7.89 (s, 1H), 8.20 (s, 1H).

22) 3-[2-(2,4-Difluorophenyl)-2-hydroxy-3-[1,2,4]-triazol-1-yl-propyl]-5-methyl-6-n-octyl-thieno[2,3-d]pyrimidin-4(3H)-one (1-A20)

1HNMR (CDCl3, 200 MHz):: 0.91 (t, J=6 Hz, 3H), 1.18-1.49 (m, 10H), 1.56-1.75 (m, 2H), 2.48 (s, 3H), 2.78 (t, J=8 Hz, 2H), 4.22 (d, J=14 Hz, 1H), 4.59 (d, J=14 Hz, 1H), 4.77 (d, J=14 Hz, 1H), 4.84 (d, J=14 Hz, 1H), 6.31 (bs, 1H), 6.80-6.92 (m, 2H), 7.54-7.72 (m, 1H), 7.90 (bs, 2H), 8.20 (bs, 1H).

23) 3-[2-(2,4-Difluorophenyl)-2-hydroxy-3-[1,2,4]-triazol-1-yl-propyl]-6-n-butyl-5-methyl-thieno[2,3-d]pyrimidin-4(3H)-one (1-A21)

1HNMR (CDCl3, 200 MHz):: 0.93 (t, J=6 Hz, 3H), 1.28-1.45 (m, 2H), 1.52-1.69 (m, 2H), 2.43 (s, 3H), 2.74 (t, J=8 Hz, 2H), 4.20 (d, J=14 Hz, 1H), 4.60 (d, J=14 Hz, 1H), 4.74 (d, J=14 Hz, 1H), 4.84 (d, J=14 Hz, 1H), 6.72-6.90 (m, 2H), 7.48-7.59 (m, 1H), 7.88 (bs, 2H), 8.34 (bs, 1H).

24) 3-[2-(2,4-Difluorophenyl)-2-hydroxy-3-[1,2,4]triazol-1-yl-propyl]-6-ethylthieno[2,3-d]pyrimidin-4(3H)-one (1-A22)

1HNMR (CDCl3, 200 MHz):: 1.35 (t, J=7 Hz, 3H), 2.87 (q, J=7 Hz, 2H), 4.27 (d, J=14 Hz, 1H), 4.60 (d, J=14 Hz, 1H), 4.72 (d, J=14 Hz, 1H), 4.83 (d, J=14 Hz, 1H), 6.26 (bs, 1H), 6.77-6.91 (m, 2H), 7.08 (s, 1H), 7.48-7.61 (m, 1H), 7.89 (s, 1H), 7.92 (s, 1H), 8.31 (s, 1H).

25) 3-[2-(2,4-Difluorophenyl)-2-hydroxy-3-[1,2,4]-triazol-1-yl-propyl]-6-(4-hydroxybutyl)-thieno[2,3-d]pyrimidin-4(3H)-one (1-A23)

1HNMR (CDCl3, 200 MHz):: 1.50-1.90 (m, 4H), 2.87 (t, J=6 Hz, 2H), 3.59 (t, J=6 Hz, 2H), 4.26 (d, J=14 Hz, 1H), 4.56 (d, J=14 Hz, 1H), 4.77 (d, J=14 Hz, 1H), 4.89 (d, J=14 Hz, 1H), 6.22 (bs, 1H), 6.72-6.92 (m, 2H), 7.07 (s, 1H), 7.35-7.50 (m, 1H), 7.76 (bs, 1H), 8.00 (s, 1H), 8.22 (bs, 1H).

26) 3-[2-(2,4-Difluorophenyl)-2-hydroxy-3-[1,2,4]triazol-1-yl-propyl]-6-(4-N-Bocaminoacetyloxybutyl)-thieno[2,3-d]pyrimidin-4(3H)-one (1-A24)

A mixture of -[2-(2,4-difluorophenyl)-2-hydroxy-3-[1,2,4]-triazol-1-yl-propyl]-6-(4-hydroxybutyl)-thieno[2,3-d]pyrimidin-4(3H)-one (500 mg, 0.895 mmol), Boc-glycine (188 mg, 1.073 mmol), DMAP (10 mg) in DCM (10 ml) was taken at 0° C. and added EDCI (257 mg, 1.34 mmol) to it and stirred for 2 hours. It was then diluted with water (10 ml), extracted with DCM (2×5 ml), dried, concentrated and purified by column chromatography to obtain the pure 3-[2-(2,4-difluorophenyl)-2-hydroxy-3-[1,2,4]triazol-1-yl-propyl]-6-(4-N-Bocaminoacetyloxybutyl)-thieno[2,3-d]pyrimidin-4(3H)-one (300 mg, 46.87%).

1HNMR (CDCl3, 200 MHz):: 1.47 (s, 9H), 1.62-1.90 (m, 4H), 2.80-2.96 (m, 2H), 3.78-3.98 (m, 2H), 4.05-4.32 (m, 3H), 4.55-4.91 (m, 3H), 5.05 (bs, 1H), 6.29 (bs, 1H), 6.73-6.89 (m, 2H), 7.12 (s, 1H), 7.50-7.65 (m, 1H), 7.92 (bs, 1H), 7.98 (s, 1H), 8.35 (bs, 1H).

27) 3-[2-(2,4-Difluorophenyl)-2-hydroxy-3-[1,2,4]-triazol-1-yl-propyl]-6-(4-aminoacetyloxybutyl)-thieno[2,3-d]pyrimidin-4(3H)-one (1-A25)

3-[2-(2,4-Difluorophenyl)-2-hydroxy-3-[1,2,4]triazol-1-yl-propyl]-6-(4-N-Bocaminoacetyloxybutyl)-thieno[2,3-d]pyrimidin-4(3H)-one (200 mg, 0.28 mmol) was dissolved in DCM (6 ml) at 0° C. Trifluoroacetic acid (0.129 ml, 191 mg, 1.68 mmol) was added to it and stirred for 4 hours. It was then diluted with water (10 ml), extracted with DCM (2×5 ml), dried, concentrated and purified by column chromatography to obtain the pure 3-[2-(2,4-difluorophenyl)-2-hydroxy-3-[1,2,4]triazol-1-yl-propyl]-6-(4-aminoacetyloxy butyl)-thieno[2,3-d]pyrimidin-4(3H)-one (100 mg, 56.81%).

1HNMR (CDCl3, 200 MHz): 1.45-1.80 (m, 4H), 2.68-2.90 (m, 2H), 4.05-4.29 (m, 4H), 4.32-4.61 (m, 3H), 4.65-4.90 (m, 3H), 5.81 (bs, 1H), 6.68-6.91 (m, 2H), 7.03 (s, 1H), 7.39-7.58 (m, 1H), 7.74 (s, 1H), 7.91 (s, 1H), 8.08 (s, 1H).

28) 3-[2-(2,4-Difluorophenyl)-2-hydroxy-3-[1,2,4]-triazol-1-yl-propyl]-6-(3-hydroxypropyl)-thieno[2,3-d]pyrimidin-4(3H)-one (1-A27)

1HNMR (CDCl3+DMSOd6, 200 MHz): 1.68-1.84 (m, 2H), 2.77 (t, J=8 Hz, 2H), 3.47 (t, J=6 Hz, 2H), 4.12 (d, J=14 Hz, 1H), 4.47 (d, J=14 Hz, 1H), 4.61 (d, J=14 Hz, 1H), 4.83 (d, J=14 Hz, 1H), 6.54-6.76 (m, 2H), 6.93 (s, 1H), 7.12-7.35 (m, 3H), 7.86 (s, 1H).

29) 3-[2-(2,4-Difluorophenyl)-2-hydroxy-3-[1,2,4]-triazol-1-yl-propyl]-6-methylthieno[2,3-d]pyrimidin-4(3H)-one (1-A28)

1HNMR (CDCl3, 200 MHz):: 2.51 (s, 3H), 4.23 (d, J=12 Hz, 1H), 4.53 (d, J=12 Hz, 1H), 4.69 (d, J=12 Hz, 1H), 4.77 (d, J=12 Hz, 1H), 6.22 (bs, 1H), 6.70-6.85 (m, 2H), 7.04 (s, 1H), 7.45-7.60 (m, 1H), 7.83 (s, 1H), 7.90 (s, 1H), 8.10 (s, 1H).

The pharmaceutical salts of the compounds of Formula (1) can be prepared by known methods and obvious modifications.

TABLE 1

Analogues of fluconazole of Formula (1)

| Compound No. | $R^1$ | $R^2$ | $R^3$ | $R^4$ | Sample No. |
|---|---|---|---|---|---|
| 1 | 2-F | 4-F | $CH_3$ | H | 1-A28 |
| 2 | 2-Cl | 4-Cl | $CH_3$ | H | |
| 3 | 2-Br | 4-Br | $CH_3$ | H | |
| 4 | 2-F | H | $CH_3$ | H | |
| 5 | 2-Cl | H | $CH_3$ | H | |
| 6 | 2-Br | H | $CH_3$ | H | |
| 7 | H | 4-F | $CH_3$ | H | |
| 8 | H | 4-Cl | $CH_3$ | H | |
| 9 | H | 4-Br | $CH_3$ | H | |
| 10 | 2-F | 4-F | H | $CH_3$ | |
| 11 | 2-Cl | 4-Cl | H | $CH_3$ | |
| 12 | 2-Br | 4-Br | H | $CH_3$ | |
| 13 | 2-F | H | H | $CH_3$ | |
| 14 | 2-Cl | H | H | $CH_3$ | |
| 15 | 2-Br | H | H | $CH_3$ | |
| 16 | H | 4-F | H | $CH_3$ | |
| 17 | H | 4-Cl | H | $CH_3$ | |
| 18 | H | 4-Br | H | $CH_3$ | |
| 19 | 2-F | 4-F | $CH_2CH_3$ | H | 1-A22 |
| 20 | 2-Cl | 4-Cl | $CH_2CH_3$ | H | |
| 21 | 2-Br | 4-Br | $CH_2CH_3$ | H | |
| 22 | 2-F | H | $CH_2CH_3$ | H | |
| 23 | 2-Cl | H | $CH_2CH_3$ | H | |
| 24 | 2-Br | H | $CH_2CH_3$ | H | |
| 25 | H | 4-F | $CH_2CH_3$ | H | |
| 26 | H | 4-Cl | $CH_2CH_3$ | H | |
| 27 | H | 4-Br | $CH_2CH_3$ | H | |
| 28 | 2-F | 4-F | H | $CH_2CH_3$ | |
| 29 | 2-Cl | 4-Cl | H | $CH_2CH_3$ | |
| 30 | 2-Br | 4-Br | H | $CH_2CH_3$ | |
| 31 | 2-F | H | H | $CH_2CH_3$ | |
| 32 | 2-Cl | H | H | $CH_2CH_3$ | |
| 33 | 2-Br | H | H | $CH_2CH_3$ | |
| 34 | H | 4-F | H | $CH_2CH_3$ | |
| 35 | H | 4-Cl | H | $CH_2CH_3$ | |
| 36 | H | 4-Br | H | $CH_2CH_3$ | |
| 37 | 2-F | 4-F | $(CH_2)_2CH_3$ | H | 1-A18 |
| 38 | 2-Cl | 4-Cl | $(CH_2)_2CH_3$ | H | |
| 39 | 2-Br | 4-Br | $(CH_2)_2CH_3$ | H | |
| 40 | 2-F | H | $(CH_2)_2CH_3$ | H | |
| 41 | 2-Cl | H | $(CH_2)_2CH_3$ | H | |
| 42 | 2-Br | H | $(CH_2)_2CH_3$ | H | |
| 43 | H | 4-F | $(CH_2)_2CH_3$ | H | |
| 44 | H | 4-Cl | $(CH_2)_2CH_3$ | H | |
| 45 | H | 4-Br | $(CH_2)_2CH_3$ | H | |
| 46 | 2-F | 4-F | H | $(CH_2)_2CH_3$ | |
| 47 | 2-Cl | 4-Cl | H | $(CH_2)_2CH_3$ | |
| 48 | 2-Br | 4-Br | H | $(CH_2)_2CH_3$ | |
| 49 | 2-F | H | H | $(CH_2)_2CH_3$ | |
| 50 | 2-Cl | H | H | $(CH_2)_2CH_3$ | |
| 51 | 2-Br | H | H | $(CH_2)_2CH_3$ | |
| 52 | H | 4-F | H | $(CH_2)_2CH_3$ | |
| 53 | H | 4-Cl | H | $(CH_2)_2CH_3$ | |
| 54 | H | 4-Br | H | $(CH_2)_2CH_3$ | |
| 55 | 2-F | 4-F | $(CH_2)_3CH_3$ | H | |
| 56 | 2-Cl | 4-Cl | $(CH_2)_3CH_3$ | H | |
| 57 | 2-Br | 4-Br | $(CH_2)_3CH_3$ | H | |
| 58 | 2-F | H | $(CH_2)_3CH_3$ | H | |
| 59 | 2-Cl | H | $(CH_2)_3CH_3$ | H | |
| 60 | 2-Br | H | $(CH_2)_3CH_3$ | H | |
| 61 | H | 4-F | $(CH_2)_3CH_3$ | H | |
| 62 | H | 4-Cl | $(CH_2)_3CH_3$ | H | |
| 63 | H | 4-Br | $(CH_2)_3CH_3$ | H | |
| 64 | 2-F | 4-F | H | $(CH_2)_3CH_3$ | |
| 65 | 2-Cl | 4-Cl | H | $(CH_2)_3CH_3$ | |
| 66 | 2-Br | 4-Br | H | $(CH_2)_3CH_3$ | |
| 67 | 2-F | H | H | $(CH_2)_3CH_3$ | |
| 68 | 2-Cl | H | H | $(CH_2)_3CH_3$ | |
| 69 | 2-Br | H | H | $(CH_2)_3CH_3$ | |
| 70 | H | 4-F | H | $(CH_2)_3CH_3$ | |

TABLE 1-continued

Analogues of fluconazole of Formula (1)

| Compound No. | R$^1$ | R$^2$ | R$^3$ | R$^4$ | Sample No. |
|---|---|---|---|---|---|
| 71 | H | 4-Cl | H | (CH$_2$)$_3$CH$_3$ | |
| 72 | H | 4-Br | H | (CH$_2$)$_3$CH$_3$ | |
| 73 | 2-F | 4-F | (CH$_2$)$_4$CH$_3$ | H | 1-A04 |
| 74 | 2-Cl | 4-Cl | (CH$_2$)$_4$CH$_3$ | H | |
| 75 | 2-Br | 4-Br | (CH$_2$)$_4$CH$_3$ | H | |
| 76 | 2-F | H | (CH$_2$)$_4$CH$_3$ | H | |
| 77 | 2-Cl | H | (CH$_2$)$_4$CH$_3$ | H | |
| 78 | 2-Br | H | (CH$_2$)$_4$CH$_3$ | H | |
| 79 | H | 4-F | (CH$_2$)$_4$CH$_3$ | H | |
| 80 | H | 4-Cl | (CH$_2$)$_4$CH$_3$ | H | |
| 81 | H | 4-Br | (CH$_2$)$_4$CH$_3$ | H | |
| 82 | 2-F | 4-F | H | (CH$_2$)$_4$CH$_3$ | |
| 83 | 2-Cl | 4-Cl | H | (CH$_2$)$_4$CH$_3$ | |
| 84 | 2-Br | 4-Br | H | (CH$_2$)$_4$CH$_3$ | |
| 85 | 2-F | H | H | (CH$_2$)$_4$CH$_3$ | |
| 86 | 2-Cl | H | H | (CH$_2$)$_4$CH$_3$ | |
| 87 | 2-Br | H | H | (CH$_2$)$_4$CH$_3$ | |
| 88 | H | 4-F | H | (CH$_2$)$_4$CH$_3$ | |
| 89 | H | 4-Cl | H | (CH$_2$)$_4$CH$_3$ | |
| 90 | H | 4-Br | H | (CH$_2$)$_4$CH$_3$ | |
| 91 | 2-F | 4-F | (CH$_2$)$_5$CH$_3$ | H | 1-A03 |
| 92 | 2-Cl | 4-Cl | (CH$_2$)$_5$CH$_3$ | H | |
| 93 | 2-Br | 4-Br | (CH$_2$)$_5$CH$_3$ | H | |
| 94 | 2-F | H | (CH$_2$)$_5$CH$_3$ | H | |
| 95 | 2-Cl | H | (CH$_2$)$_5$CH$_3$ | H | |
| 96 | 2-Br | H | (CH$_2$)$_5$CH$_3$ | H | |
| 97 | H | 4-F | (CH$_2$)$_5$CH$_3$ | H | |
| 98 | H | 4-Cl | (CH$_2$)$_5$CH$_3$ | H | |
| 99 | H | 4-Br | (CH$_2$)$_5$CH$_3$ | H | |
| 100 | 2-F | 4-F | H | (CH$_2$)$_5$CH$_3$ | |
| 101 | 2-Cl | 4-Cl | H | (CH$_2$)$_5$CH$_3$ | |
| 102 | 2-Br | 4-Br | H | (CH$_2$)$_5$CH$_3$ | |
| 103 | 2-F | H | H | (CH$_2$)$_5$CH$_3$ | |
| 104 | 2-Cl | H | H | (CH$_2$)$_5$CH$_3$ | |
| 105 | 2-Br | H | H | (CH$_2$)$_5$CH$_3$ | |
| 106 | H | 4-F | H | (CH$_2$)$_5$CH$_3$ | |
| 107 | H | 4-Cl | H | (CH$_2$)$_5$CH$_3$ | |
| 108 | H | 4-Br | H | (CH$_2$)$_5$CH$_3$ | |
| 109 | 2-F | 4-F | (CH$_2$)$_6$CH$_3$ | H | 1-A06 |
| 110 | 2-Cl | 4-Cl | (CH$_2$)$_6$CH$_3$ | H | |
| 111 | 2-Br | 4-Br | (CH$_2$)$_6$CH$_3$ | H | |
| 112 | 2-F | H | (CH$_2$)$_6$CH$_3$ | H | |
| 113 | 2-Cl | H | (CH$_2$)$_6$CH$_3$ | H | |
| 114 | 2-Br | H | (CH$_2$)$_6$CH$_3$ | H | |
| 115 | H | 4-F | (CH$_2$)$_6$CH$_3$ | H | |
| 116 | H | 4-Cl | (CH$_2$)$_6$CH$_3$ | H | |
| 117 | H | 4-Br | (CH$_2$)$_6$CH$_3$ | H | |
| 118 | 2-F | 4-F | H | (CH$_2$)$_6$CH$_3$ | |
| 119 | 2-Cl | 4-Cl | H | (CH$_2$)$_6$CH$_3$ | |
| 120 | 2-Br | 4-Br | H | (CH$_2$)$_6$CH$_3$ | |
| 121 | 2-F | H | H | (CH$_2$)$_6$CH$_3$ | |
| 122 | 2-Cl | H | H | (CH$_2$)$_6$CH$_3$ | |
| 123 | 2-Br | H | H | (CH$_2$)$_6$CH$_3$ | |
| 124 | H | 4-F | H | (CH$_2$)$_6$CH$_3$ | |
| 125 | H | 4-Cl | H | (CH$_2$)$_6$CH$_3$ | |
| 126 | H | 4-Br | H | (CH$_2$)$_6$CH$_3$ | |
| 127 | 2-F | 4-F | (CH$_2$)$_7$CH$_3$ | H | |
| 128 | 2-Cl | 4-Cl | (CH$_2$)$_7$CH$_3$ | H | |
| 129 | 2-Br | 4-Br | (CH$_2$)$_7$CH$_3$ | H | |
| 130 | 2-F | H | (CH$_2$)$_7$CH$_3$ | H | |
| 131 | 2-Cl | H | (CH$_2$)$_7$CH$_3$ | H | |
| 132 | 2-Br | H | (CH$_2$)$_7$CH$_3$ | H | |
| 133 | H | 4-F | (CH$_2$)$_7$CH$_3$ | H | |
| 134 | H | 4-Cl | (CH$_2$)$_7$CH$_3$ | H | |
| 135 | H | 4-Br | (CH$_2$)$_7$CH$_3$ | H | |
| 136 | 2-F | 4-F | H | (CH$_2$)$_7$CH$_3$ | |
| 137 | 2-Cl | 4-Cl | H | (CH$_2$)$_7$CH$_3$ | |
| 138 | 2-Br | 4-Br | H | (CH$_2$)$_7$CH$_3$ | |
| 139 | 2-F | H | H | (CH$_2$)$_7$CH$_3$ | |
| 140 | 2-Cl | H | H | (CH$_2$)$_7$CH$_3$ | |
| 141 | 2-Br | H | H | (CH$_2$)$_7$CH$_3$ | |
| 142 | H | 4-F | H | (CH$_2$)$_7$CH$_3$ | |
| 143 | H | 4-Cl | H | (CH$_2$)$_7$CH$_3$ | |
| 144 | H | 4-Br | H | (CH$_2$)$_7$CH$_3$ | |
| 145 | 2-F | 4-F | (CH$_2$)$_8$CH$_3$ | H | 1-A17 |

TABLE 1-continued

Analogues of fluconazole of Formula (1)

| Compound No. | $R^1$ | $R^2$ | $R^3$ | $R^4$ | Sample No. |
|---|---|---|---|---|---|
| 146 | 2-Cl | 4-Cl | $(CH_2)_8CH_3$ | H | |
| 147 | 2-Br | 4-Br | $(CH_2)_8CH_3$ | H | |
| 148 | 2-F | H | $(CH_2)_8CH_3$ | H | |
| 149 | 2-Cl | H | $(CH_2)_8CH_3$ | H | |
| 150 | 2-Br | H | $(CH_2)_8CH_3$ | H | |
| 151 | H | 4-F | $(CH_2)_8CH_3$ | H | |
| 152 | H | 4-Cl | $(CH_2)_8CH_3$ | H | |
| 153 | H | 4-Br | $(CH_2)_8CH_3$ | H | |
| 154 | 2-F | 4-F | H | $(CH_2)_8CH_3$ | |
| 155 | 2-Cl | 4-Cl | H | $(CH_2)_8CH_3$ | |
| 156 | 2-Br | 4-Br | H | $(CH_2)_8CH_3$ | |
| 157 | 2-F | H | H | $(CH_2)_8CH_3$ | |
| 158 | 2-Cl | H | H | $(CH_2)_8CH_3$ | |
| 159 | 2-Br | H | H | $(CH_2)_8CH_3$ | |
| 160 | H | 4-F | H | $(CH_2)_8CH_3$ | |
| 161 | H | 4-Cl | H | $(CH_2)_8CH_3$ | |
| 162 | H | 4-Br | H | $(CH_2)_8CH_3$ | |
| 163 | 2-F | 4-F | $(CH_2)_9CH_3$ | H | 1-A16 |
| 164 | 2-Cl | 4-Cl | $(CH_2)_9CH_3$ | H | |
| 165 | 2-Br | 4-Br | $(CH_2)_9CH_3$ | H | |
| 166 | 2-F | H | $(CH_2)_9CH_3$ | H | |
| 167 | 2-Cl | H | $(CH_2)_9CH_3$ | H | |
| 168 | 2-Br | H | $(CH_2)_9CH_3$ | H | |
| 169 | H | 4-F | $(CH_2)_9CH_3$ | H | |
| 170 | H | 4-Cl | $(CH_2)_9CH_3$ | H | |
| 171 | H | 4-Br | $(CH_2)_9CH_3$ | H | |
| 172 | 2-F | 4-F | H | $(CH_2)_9CH_3$ | |
| 173 | 2-Cl | 4-Cl | H | $(CH_2)_9CH_3$ | |
| 174 | 2-Br | 4-Br | H | $(CH_2)_9CH_3$ | |
| 175 | 2-F | H | H | $(CH_2)_9CH_3$ | |
| 176 | 2-Cl | H | H | $(CH_2)_9CH_3$ | |
| 177 | 2-Br | H | H | $(CH_2)_9CH_3$ | |
| 178 | H | 4-F | H | $(CH_2)_9CH_3$ | |
| 179 | H | 4-Cl | H | $(CH_2)_9CH_3$ | |
| 180 | H | 4-Br | H | $(CH_2)_9CH_3$ | |
| 181 | 2-F | 4-F | $CH_3$ | $CH_3$ | |
| 182 | 2-Cl | 4-Cl | $CH_3$ | $CH_3$ | |
| 183 | 2-Br | 4-Br | $CH_3$ | $CH_3$ | |
| 184 | 2-F | H | $CH_3$ | $CH_3$ | |
| 185 | 2-Cl | H | $CH_3$ | $CH_3$ | |
| 186 | 2-Br | H | $CH_3$ | $CH_3$ | |
| 187 | H | 4-F | $CH_3$ | $CH_3$ | |
| 188 | H | 4-Cl | $CH_3$ | $CH_3$ | |
| 189 | H | 4-Br | $CH_3$ | $CH_3$ | |
| 190 | 2-F | 4-F | $CH_3$ | $CH_2CH_3$ | |
| 191 | 2-Cl | 4-Cl | $CH_3$ | $CH_2CH_3$ | |
| 192 | 2-Br | 4-Br | $CH_3$ | $CH_2CH_3$ | |
| 193 | 2-F | H | $CH_3$ | $CH_2CH_3$ | |
| 194 | 2-Cl | H | $CH_3$ | $CH_2CH_3$ | |
| 195 | 2-Br | H | $CH_3$ | $CH_2CH_3$ | |
| 196 | H | 4-F | $CH_3$ | $CH_2CH_3$ | |
| 197 | H | 4-Cl | $CH_3$ | $CH_2CH_3$ | |
| 198 | H | 4-Br | $CH_3$ | $CH_2CH_3$ | |
| 199 | 2-F | 4-F | $CH_3$ | $(CH_2)_2CH_3$ | |
| 200 | 2-Cl | 4-Cl | $CH_3$ | $(CH_2)_2CH_3$ | |
| 201 | 2-Br | 4-Br | $CH_3$ | $(CH_2)_2CH_3$ | |
| 202 | 2-F | H | $CH_3$ | $(CH_2)_2CH_3$ | |
| 203 | 2-Cl | H | $CH_3$ | $(CH_2)_2CH_3$ | |
| 204 | 2-Br | H | $CH_3$ | $(CH_2)_2CH_3$ | |
| 205 | H | 4-F | $CH_3$ | $(CH_2)_2CH_3$ | |
| 206 | H | 4-Cl | $CH_3$ | $(CH_2)_2CH_3$ | |
| 207 | H | 4-Br | $CH_3$ | $(CH_2)_2CH_3$ | |
| 208 | 2-F | 4-F | $CH_3$ | $(CH_2)_3CH_3$ | |
| 209 | 2-Cl | 4-Cl | $CH_3$ | $(CH_2)_3CH_3$ | |
| 210 | 2-Br | 4-Br | $CH_3$ | $(CH_2)_3CH_3$ | |
| 211 | 2-F | H | $CH_3$ | $(CH_2)_3CH_3$ | |
| 212 | 2-Cl | H | $CH_3$ | $(CH_2)_3CH_3$ | |
| 213 | 2-Br | H | $CH_3$ | $(CH_2)_3CH_3$ | |
| 214 | H | 4-F | $CH_3$ | $(CH_2)_3CH_3$ | |
| 215 | H | 4-Cl | $CH_3$ | $(CH_2)_3CH_3$ | |
| 216 | H | 4-Br | $CH_3$ | $(CH_2)_3CH_3$ | |
| 217 | 2-F | 4-F | $CH_3$ | $(CH_2)_4CH_3$ | 1-A08 |
| 218 | 2-Cl | 4-Cl | $CH_3$ | $(CH_2)_4CH_3$ | |
| 219 | 2-Br | 4-Br | $CH_3$ | $(CH_2)_4CH_3$ | |
| 220 | 2-F | H | $CH_3$ | $(CH_2)_4CH_3$ | |

TABLE 1-continued

Analogues of fluconazole of Formula (1)

| Compound No. | R¹ | R² | R³ | R⁴ | Sample No. |
|---|---|---|---|---|---|
| 221 | 2-Cl | H | CH$_3$ | (CH$_2$)$_4$CH$_3$ | |
| 222 | 2-Br | H | CH$_3$ | (CH$_2$)$_4$CH$_3$ | |
| 223 | H | 4-F | CH$_3$ | (CH$_2$)$_4$CH$_3$ | |
| 224 | H | 4-Cl | CH$_3$ | (CH$_2$)$_4$CH$_3$ | |
| 225 | H | 4-Br | CH$_3$ | (CH$_2$)$_4$CH$_3$ | |
| 226 | 2-F | 4-F | CH$_3$ | (CH$_2$)$_5$CH$_3$ | |
| 227 | 2-Cl | 4-Cl | CH$_3$ | (CH$_2$)$_5$CH$_3$ | |
| 228 | 2-Br | 4-Br | CH$_3$ | (CH$_2$)$_5$CH$_3$ | |
| 229 | 2-F | H | CH$_3$ | (CH$_2$)$_5$CH$_3$ | |
| 230 | 2-Cl | H | CH$_3$ | (CH$_2$)$_5$CH$_3$ | |
| 231 | 2-Br | H | CH$_3$ | (CH$_2$)$_5$CH$_3$ | |
| 232 | H | 4-F | CH$_3$ | (CH$_2$)$_5$CH$_3$ | |
| 233 | H | 4-Cl | CH$_3$ | (CH$_2$)$_5$CH$_3$ | |
| 234 | H | 4-Br | CH$_3$ | (CH$_2$)$_5$CH$_3$ | |
| 235 | 2-F | 4-F | CH$_3$ | (CH$_2$)$_6$CH$_3$ | |
| 236 | 2-Cl | 4-Cl | CH$_3$ | (CH$_2$)$_6$CH$_3$ | |
| 237 | 2-Br | 4-Br | CH$_3$ | (CH$_2$)$_5$CH$_3$ | |
| 238 | 2-F | H | CH$_3$ | (CH$_2$)$_6$CH$_3$ | |
| 239 | 2-Cl | H | CH$_3$ | (CH$_2$)$_6$CH$_3$ | |
| 240 | 2-Br | H | CH$_3$ | (CH$_2$)$_6$CH$_3$ | |
| 241 | H | 4-F | CH$_3$ | (CH$_2$)$_6$CH$_3$ | |
| 242 | H | 4-Cl | CH$_3$ | (CH$_2$)$_6$CH$_3$ | |
| 243 | H | 4-Br | CH$_3$ | (CH$_2$)$_6$CH$_3$ | |
| 244 | 2-F | 4-F | CH$_3$ | (CH$_2$)$_7$CH$_3$ | |
| 245 | 2-Cl | 4-Cl | CH$_3$ | (CH$_2$)$_7$CH$_3$ | |
| 246 | 2-Br | 4-Br | CH$_3$ | (CH$_2$)$_7$CH$_3$ | |
| 247 | 2-F | H | CH$_3$ | (CH$_2$)$_7$CH$_3$ | |
| 248 | 2-Cl | H | CH$_3$ | (CH$_2$)$_7$CH$_3$ | |
| 249 | 2-Br | H | CH$_3$ | (CH$_2$)$_7$CH$_3$ | |
| 250 | H | 4-F | CH$_3$ | (CH$_2$)$_7$CH$_3$ | |
| 251 | H | 4-Cl | CH$_3$ | (CH$_2$)$_7$CH$_3$ | |
| 252 | H | 4-Br | CH$_3$ | (CH$_2$)$_7$CH$_3$ | |
| 253 | 2-F | 4-F | CH$_3$ | (CH$_2$)$_8$CH$_3$ | |
| 254 | 2-Cl | 4-Cl | CH$_3$ | (CH$_2$)$_8$CH$_3$ | |
| 255 | 2-Br | 4-Br | CH$_3$ | (CH$_2$)$_8$CH$_3$ | |
| 256 | 2-F | H | CH$_3$ | (CH$_2$)$_3$CH$_3$ | |
| 257 | 2-Cl | H | CH$_3$ | (CH$_2$)$_8$CH$_3$ | |
| 258 | 2-Br | H | CH$_3$ | (CH$_2$)$_8$CH$_3$ | |
| 259 | H | 4-F | CH$_3$ | (CH$_2$)$_8$CH$_3$ | |
| 260 | H | 4-Cl | CH$_3$ | (CH$_2$)$_8$CH$_3$ | |
| 261 | H | 4-Br | CH$_3$ | (CH$_2$)$_8$CH$_3$ | |
| 262 | 2-F | 4-F | CH$_2$CH$_3$ | CH$_3$ | |
| 263 | 2-Cl | 4-Cl | CH$_2$CH$_3$ | CH$_3$ | |
| 264 | 2-Br | 4-Br | CH$_2$CH$_3$ | CH$_3$ | |
| 265 | 2-F | H | CH$_2$CH$_3$ | CH$_3$ | |
| 266 | 2-Cl | H | CH$_2$CH$_3$ | CH$_3$ | |
| 267 | 2-Br | H | CH$_2$CH$_3$ | CH$_3$ | |
| 268 | H | 4-F | CH$_2$CH$_3$ | CH$_3$ | |
| 269 | H | 4-Cl | CH$_2$CH$_3$ | CH$_3$ | |
| 270 | H | 4-Br | CH$_2$CH$_3$ | CH$_3$ | |
| 271 | 2-F | 4-F | (CH$_2$)$_2$CH$_3$ | CH$_3$ | |
| 272 | 2-Cl | 4-Cl | (CH$_2$)$_2$CH$_3$ | CH$_3$ | |
| 273 | 2-Br | 4-Br | (CH$_2$)$_2$CH$_3$ | CH$_3$ | |
| 274 | 2-F | H | (CH$_2$)$_2$CH$_3$ | CH$_3$ | |
| 275 | 2-Cl | H | (CH$_2$)$_2$CH$_3$ | CH$_3$ | |
| 276 | 2-Br | H | (CH$_2$)$_2$CH$_3$ | CH$_3$ | |
| 277 | H | 4-F | (CH$_2$)$_2$CH$_3$ | CH$_3$ | |
| 278 | H | 4-Cl | (CH$_2$)$_2$CH$_3$ | CH$_3$ | |
| 279 | H | 4-Br | (CH$_2$)$_2$CH$_3$ | CH$_3$ | |
| 280 | 2-F | 4-F | (CH$_2$)$_3$CH$_3$ | CH$_3$ | |
| 281 | 2-Cl | 4-Cl | (CH$_2$)$_3$CH$_3$ | CH$_3$ | |
| 282 | 2-Br | 4-Br | (CH$_2$)$_3$CH$_3$ | CH$_3$ | |
| 283 | 2-F | H | (CH$_2$)$_3$CH$_3$ | CH$_3$ | |
| 284 | 2-Cl | H | (CH$_2$)$_3$CH$_3$ | CH$_3$ | |
| 285 | 2-Br | H | (CH$_2$)$_3$CH$_3$ | CH$_3$ | |
| 286 | H | 4-F | (CH$_2$)$_3$CH$_3$ | CH$_3$ | |
| 287 | H | 4-Cl | (CH$_2$)$_3$CH$_3$ | CH$_3$ | |
| 288 | H | 4-Br | (CH$_2$)$_3$CH$_3$ | CH$_3$ | |
| 289 | 2-F | 4-F | (CH$_2$)$_4$CH$_3$ | CH$_3$ | 1-A11 |
| 290 | 2-Cl | 4-Cl | (CH$_2$)$_4$CH$_3$ | CH$_3$ | |
| 291 | 2-Br | 4-Br | (CH$_2$)$_4$CH$_3$ | CH$_3$ | |
| 292 | 2-F | H | (CH$_2$)$_4$CH$_3$ | CH$_3$ | |
| 293 | 2-Cl | H | (CH$_2$)$_4$CH$_3$ | CH$_3$ | |
| 294 | 2-Br | H | (CH$_2$)$_4$CH$_3$ | CH$_3$ | |
| 295 | H | 4-F | (CH$_2$)$_4$CH$_3$ | CH$_3$ | |

TABLE 1-continued

Analogues of fluconazole of Formula (1)

| Compound No. | R¹ | R² | R³ | R⁴ | Sample No. |
|---|---|---|---|---|---|
| 296 | H | 4-Cl | (CH$_2$)$_4$CH$_3$ | CH$_3$ | |
| 297 | H | 4-Br | (CH$_2$)$_4$CH$_3$ | CH$_3$ | |
| 298 | 2-F | 4-F | (CH$_2$)$_5$CH$_3$ | CH$_3$ | 1-A10 |
| 299 | 2-Cl | 4-Cl | (CH$_2$)$_5$CH$_3$ | CH$_3$ | |
| 300 | 2-Br | 4-Br | (CH$_2$)$_5$CH$_3$ | CH$_3$ | |
| 301 | 2-F | H | (CH$_2$)$_5$CH$_3$ | CH$_3$ | |
| 302 | 2-Cl | H | (CH$_2$)$_5$CH$_3$ | CH$_3$ | |
| 303 | 2-Br | H | (CH$_2$)$_5$CH$_3$ | CH$_3$ | |
| 304 | H | 4-F | (CH$_2$)$_5$CH$_3$ | CH$_3$ | |
| 305 | H | 4-Cl | (CH$_2$)$_5$CH$_3$ | CH$_3$ | |
| 306 | H | 4-Br | (CH$_2$)$_5$CH$_3$ | CH$_3$ | |
| 307 | 2-F | 4-F | (CH$_2$)$_6$CH$_3$ | CH$_3$ | |
| 308 | 2-Cl | 4-Cl | (CH$_2$)$_6$CH$_3$ | CH$_3$ | |
| 309 | 2-Br | 4-Br | (CH$_2$)$_6$CH$_3$ | CH$_3$ | |
| 310 | 2-F | H | (CH$_2$)$_6$CH$_3$ | CH$_3$ | |
| 311 | 2-Cl | H | (CH$_2$)$_6$CH$_3$ | CH$_3$ | |
| 312 | 2-Br | H | (CH$_2$)$_6$CH$_3$ | CH$_3$ | |
| 313 | H | 4-F | (CH$_2$)$_6$CH$_3$ | CH$_3$ | |
| 314 | H | 4-Cl | (CH$_2$)$_6$CH$_3$ | CH$_3$ | |
| 315 | H | 4-Br | (CH$_2$)$_6$CH$_3$ | CH$_3$ | |
| 316 | 2-F | 4-F | (CH$_2$)$_7$CH$_3$ | CH$_3$ | |
| 317 | 2-Cl | 4-Cl | (CH$_2$)$_7$CH$_3$ | CH$_3$ | |
| 318 | 2-Br | 4-Br | (CH$_2$)$_7$CH$_3$ | CH$_3$ | |
| 319 | 2-F | H | (CH$_2$)$_7$CH$_3$ | CH$_3$ | |
| 320 | 2-Cl | H | (CH$_2$)$_7$CH$_3$ | CH$_3$ | |
| 321 | 2-Br | H | (CH$_2$)$_7$CH$_3$ | CH$_3$ | |
| 322 | H | 4-F | (CH$_2$)$_7$CH$_3$ | CH$_3$ | |
| 323 | H | 4-Cl | (CH$_2$)$_7$CH$_3$ | CH$_3$ | |
| 324 | H | 4-Br | (CH$_2$)$_7$CH$_3$ | CH$_3$ | |
| 325 | 2-F | 4-F | (CH$_2$)$_8$CH$_3$ | CH$_3$ | |
| 326 | 2-Cl | 4-Cl | (CH$_2$)$_8$CH$_3$ | CH$_3$ | |
| 327 | 2-Br | 4-Br | (CH$_2$)$_8$CH$_3$ | CH$_3$ | |
| 328 | 2-F | H | (CH$_2$)$_8$CH$_3$ | CH$_3$ | |
| 329 | 2-Cl | H | (CH$_2$)$_8$CH$_3$ | CH$_3$ | |
| 330 | 2-Br | H | (CH$_2$)$_8$CH$_3$ | CH$_3$ | |
| 331 | H | 4-F | (CH$_2$)$_8$CH$_3$ | CH$_3$ | |
| 332 | H | 4-Cl | (CH$_2$)$_8$CH$_3$ | CH$_3$ | |
| 333 | H | 4-Br | (CH$_2$)$_8$CH$_3$ | CH$_3$ | |
| 334 | 2-F | 4-F | —(CH$_2$)$_3$— | =R³ | 1-A07 |
| 335 | 2-Cl | 4-Cl | —(CH$_2$)$_3$— | =R³ | |
| 336 | 2-Br | 4-Br | —(CH$_2$)$_3$— | =R³ | |
| 337 | 2-F | H | —(CH$_2$)$_3$— | =R³ | |
| 338 | 2-Cl | H | —(CH$_2$)$_3$— | =R³ | |
| 339 | 2-Br | H | —(CH$_2$)$_3$— | =R³ | |
| 340 | H | 4-F | —(CH$_2$)$_3$— | =R³ | |
| 341 | H | 4-Cl | —(CH$_2$)$_3$— | =R³ | |
| 342 | H | 4-Br | —(CH$_2$)$_3$— | =R³ | |
| 343 | 2-F | 4-F | —(CH$_2$)$_4$— | =R³ | 1-A09 |
| 344 | 2-Cl | 4-Cl | —(CH$_2$)$_4$— | =R³ | |
| 345 | 2-Br | 4-Br | —(CH$_2$)$_4$— | =R³ | |
| 346 | 2-F | H | —(CH$_2$)$_4$— | =R³ | |
| 347 | 2-Cl | H | —(CH$_2$)$_4$— | =R³ | |
| 348 | 2-Br | H | —(CH$_2$)$_4$— | =R³ | |
| 349 | H | 4-F | —(CH$_2$)$_4$— | =R³ | |
| 350 | H | 4-Cl | —(CH$_2$)$_4$— | =R³ | |
| 351 | H | 4-Br | —(CH$_2$)$_4$— | =R³ | |
| 352 | 2-F | 4-F | —(CH$_2$)$_5$— | =R³ | |
| 353 | 2-Cl | 4-Cl | —(CH$_2$)$_5$— | =R³ | |
| 354 | 2-Br | 4-Br | —(CH$_2$)$_5$— | =R³ | |
| 355 | 2-F | H | —(CH$_2$)$_5$— | =R³ | |
| 356 | 2-Cl | H | —(CH$_2$)$_5$— | =R³ | |
| 357 | 2-Br | H | —(CH$_2$)$_5$— | =R³ | |
| 358 | H | 4-F | —(CH$_2$)$_5$— | =R³ | |
| 359 | H | 4-Cl | —(CH$_2$)$_5$— | =R³ | |
| 360 | H | 4-Br | —(CH$_2$)$_5$— | =R³ | |
| 361 | 2-F | 4-F | —(CH$_2$)$_6$— | =R³ | |
| 362 | 2-Cl | 4-Cl | —(CH$_2$)$_6$— | =R³ | |
| 363 | 2-Br | 4-Br | —(CH$_2$)$_6$— | =R³ | |
| 364 | 2-F | H | —(CH$_2$)$_6$— | =R³ | |
| 365 | 2-Cl | H | —(CH$_2$)$_6$— | =R³ | |
| 366 | 2-Br | H | —(CH$_2$)$_6$— | =R³ | |
| 367 | H | 4-F | —(CH$_2$)$_6$— | =R³ | |
| 368 | H | 4-Cl | —(CH$_2$)$_6$— | =R³ | |
| 369 | H | 4-Br | —(CH$_2$)$_6$— | =R³ | |
| 370 | 2-F | 4-F | —(CH$_2$)$_7$— | =R³ | |

TABLE 1-continued

Analogues of fluconazole of Formula (1)

| Compound No. | R¹ | R² | R³ | R⁴ | Sample No. |
|---|---|---|---|---|---|
| 371 | 2-Cl | 4-Cl | —(CH$_2$)$_7$— | =R³ | |
| 372 | 2-Br | 4-Br | —(CH$_2$)$_7$— | =R³ | |
| 373 | 2-F | H | —(CH$_2$)$_7$— | =R³ | |
| 374 | 2-Cl | H | —(CH$_2$)$_7$— | =R³ | |
| 375 | 2-Br | H | —(CH$_2$)$_7$— | =R³ | |
| 376 | H | 4-F | —(CH$_2$)$_7$— | =R³ | |
| 377 | H | 4-Cl | —(CH$_2$)$_7$— | =R³ | |
| 378 | H | 4-Br | —(CH$_2$)$_7$— | =R³ | |
| 379 | 2-F | 4-F | —(CH$_2$)$_8$— | =R³ | |
| 380 | 2-Cl | 4-Cl | —(CH$_2$)$_8$— | =R³ | |
| 381 | 2-Br | 4-Br | —(CH$_2$)$_8$— | =R³ | |
| 382 | 2-F | H | —(CH$_2$)$_8$— | =R³ | |
| 383 | 2-Cl | H | —(CH$_2$)$_8$— | =R³ | |
| 384 | 2-Br | H | —(CH$_2$)$_8$— | =R³ | |
| 385 | H | 4-F | —(CH$_2$)$_8$— | =R³ | |
| 386 | H | 4-Cl | —(CH$_2$)$_8$— | =R³ | |
| 387 | H | 4-Br | —(CH$_2$)$_8$— | =R³ | |
| 388 | 2-F | 4-F | —(CH$_2$)$_9$— | =R³ | |
| 389 | 2-Cl | 4-Cl | —(CH$_2$)$_9$— | =R³ | |
| 390 | 2-Br | 4-Br | —(CH$_2$)$_9$— | =R³ | |
| 391 | 2-F | H | —(CH$_2$)$_9$— | =R³ | |
| 392 | 2-Cl | H | —(CH$_2$)$_9$— | =R³ | |
| 393 | 2-Br | H | —(CH$_2$)$_9$— | =R³ | |
| 394 | H | 4-F | —(CH$_2$)$_9$— | =R³ | |
| 395 | H | 4-Cl | —(CH$_2$)$_9$— | =R³ | |
| 396 | H | 4-Br | —(CH$_2$)$_9$— | =R³ | |
| 397 | 2-F | 4-F | —(CH$_2$)$_{10}$— | =R³ | |
| 398 | 2-Cl | 4-Cl | —(CH$_2$)$_{10}$— | =R³ | |
| 399 | 2-Br | 4-Br | —(CH$_2$)$_{10}$— | =R³ | |
| 400 | 2-F | H | —(CH$_2$)$_{10}$— | =R³ | |
| 401 | 2-Cl | H | —(CH$_2$)$_{10}$— | =R³ | |
| 402 | 2-Br | H | —(CH$_2$)$_{10}$— | =R³ | |
| 403 | H | 4-F | —(CH$_2$)$_{10}$— | =R³ | |
| 404 | H | 4-Cl | —(CH$_2$)$_{10}$— | =R³ | |
| 405 | H | 4-Br | —(CH$_2$)$_{10}$— | =R³ | 1-A19 |
| 406 | 2-F | 4-F | CH$_2$OH | H | |
| 407 | 2-Cl | 4-Cl | CH$_2$OH | H | |
| 408 | 2-Br | 4-Br | CH$_2$OH | H | |
| 409 | 2-F | H | CH$_2$OH | H | |
| 410 | 2-Cl | H | CH$_2$OH | H | |
| 411 | 2-Br | H | CH$_2$OH | H | |
| 412 | H | 4-F | CH$_2$OH | H | |
| 413 | H | 4-Cl | CH$_2$OH | H | |
| 414 | H | 4-Br | CH$_2$OH | H | |
| 415 | 2-F | 4-F | CH$_2$CH$_2$OH | H | |
| 416 | 2-Cl | 4-Cl | CH$_2$CH$_2$OH | H | |
| 417 | 2-Br | 4-Br | CH$_2$CH$_2$OH | H | |
| 418 | 2-F | H | CH$_2$CH$_2$OH | H | |
| 419 | 2-Cl | H | CH$_2$CH$_2$OH | H | |
| 420 | 2-Br | H | CH$_2$CH$_2$OH | H | |
| 421 | H | 4-F | CH$_2$CH$_2$OH | H | |
| 422 | H | 4-Cl | CH$_2$CH$_2$OH | H | |
| 423 | H | 4-Br | CH$_2$CH$_2$OH | H | |
| 424 | 2-F | 4-F | (CH$_2$)$_2$CH$_2$OH | H | 1-A 27 |
| 425 | 2-Cl | 4-Cl | (CH$_2$)$_2$CH$_2$OH | H | |
| 426 | 2-Br | 4-Br | (CH$_2$)$_2$CH$_2$OH | H | |
| 427 | 2-F | H | (CH$_2$)$_2$CH$_2$OH | H | |
| 428 | 2-Cl | H | (CH$_2$)$_2$CH$_2$OH | H | |
| 429 | 2-Br | H | (CH$_2$)$_2$CH$_2$OH | H | |
| 430 | H | 4-F | (CH$_2$)$_2$CH$_2$OH | H | |
| 431 | H | 4-Cl | (CH$_2$)$_2$CH$_2$OH | H | |
| 432 | H | 4-Br | (CH$_2$)$_2$CH$_2$OH | H | |
| 433 | 2-F | 4-F | (CH$_2$)$_3$CH$_2$OH | H | 1-A 23 |
| 434 | 2-Cl | 4-Cl | (CH$_2$)$_3$CH$_2$OH | H | |
| 435 | 2-Br | 4-Br | (CH$_2$)$_3$CH$_2$OH | H | |
| 436 | 2-F | H | (CH$_2$)$_3$CH$_2$OH | H | |
| 437 | 2-Cl | H | (CH$_2$)$_3$CH$_2$OH | H | |
| 438 | 2-Br | H | (CH$_2$)$_3$CH$_2$OH | H | |
| 439 | H | 4-F | (CH$_2$)$_3$CH$_2$OH | H | |
| 440 | H | 4-Cl | (CH$_2$)$_3$CH$_2$OH | H | |
| 441 | H | 4-Br | (CH$_2$)$_3$CH$_2$OH | H | |
| 442 | 2-F | 4-F | (CH$_2$)$_4$CH$_2$OH | H | |
| 443 | 2-Cl | 4-Cl | (CH$_2$)$_4$CH$_2$OH | H | |
| 444 | 2-Br | 4-Br | (CH$_2$)$_4$CH$_2$OH | H | |
| 445 | 2-F | H | (CH$_2$)$_4$CH$_2$OH | H | |

TABLE 1-continued

Analogues of fluconazole of Formula (1)

| Compound No. | R¹ | R² | R³ | R⁴ | Sample No. |
|---|---|---|---|---|---|
| 446 | 2-Cl | H | (CH$_2$)$_4$CH$_2$OH | H | |
| 447 | 2-Br | H | (CH$_2$)$_4$CH$_2$OH | H | |
| 448 | H | 4-F | (CH$_2$)$_4$CH$_2$OH | H | |
| 449 | H | 4-Cl | (CH$_2$)$_4$CH$_2$OH | H | |
| 450 | H | 4-Br | (CH$_2$)$_4$CH$_2$OH | H | |
| 451 | 2-F | 4-F | (CH$_2$)$_5$CH$_2$OH | H | |
| 452 | 2-Cl | 4-Cl | (CH$_2$)$_5$CH$_2$OH | H | |
| 453 | 2-Br | 4-Br | (CH$_2$)$_5$CH$_2$OH | H | |
| 454 | 2-F | H | (CH$_2$)$_5$CH$_2$OH | H | |
| 455 | 2-Cl | H | (CH$_2$)$_5$CH$_2$OH | H | |
| 456 | 2-Br | H | (CH$_2$)$_5$CH$_2$OH | H | |
| 457 | H | 4-F | (CH$_2$)$_5$CH$_2$OH | H | |
| 458 | H | 4-Cl | (CH$_2$)$_5$CH$_2$OH | H | |
| 459 | H | 4-Br | (CH$_2$)$_5$CH$_2$OH | H | |
| 460 | 2-F | 4-F | (CH$_2$)$_6$CH$_2$OH | H | 1-A13 |
| 461 | 2-Cl | 4-Cl | (CH$_2$)$_6$CH$_2$OH | H | |
| 462 | 2-Br | 4-Br | (CH$_2$)$_6$CH$_2$OH | H | |
| 463 | 2-F | H | (CH$_2$)$_6$CH$_2$OH | H | |
| 464 | 2-Cl | H | (CH$_2$)$_6$CH$_2$OH | H | |
| 465 | 2-Br | H | (CH$_2$)$_6$CH$_2$OH | H | |
| 466 | H | 4-F | (CH$_2$)$_6$CH$_2$OH | H | |
| 467 | H | 4-Cl | (CH$_2$)$_6$CH$_2$OH | H | |
| 468 | H | 4-Br | (CH$_2$)$_6$CH$_2$OH | H | |
| 469 | 2-F | 4-F | (CH$_2$)$_7$CH$_2$OH | H | |
| 470 | 2-Cl | 4-Cl | (CH$_2$)$_7$CH$_2$OH | H | |
| 471 | 2-Br | 4-Br | (CH$_2$)$_7$CH$_2$OH | H | |
| 472 | 2-F | H | (CH$_2$)$_7$CH$_2$OH | H | |
| 473 | 2-Cl | H | (CH$_2$)$_7$CH$_2$OH | H | |
| 474 | 2-Br | H | (CH$_2$)$_7$CH$_2$OH | H | |
| 475 | H | 4-F | (CH$_2$)$_7$CH$_2$OH | H | |
| 476 | H | 4-Cl | (CH$_2$)$_7$CH$_2$OH | H | |
| 477 | H | 4-Br | (CH$_2$)$_7$CH$_2$OH | H | |
| 478 | 2-F | 4-F | (CH$_2$)$_n$CH$_2$OAc | H | |
| 479 | 2-Cl | 4-Cl | (CH$_2$)$_n$CH$_2$OAc | H | |
| 480 | 2-Br | 4-Br | (CH$_2$)$_n$CH$_2$OAc | H | |
| 481 | 2-F | H | (CH$_2$)$_n$CH$_2$OAc | H | |
| 482 | 2-Cl | H | (CH$_2$)$_n$CH$_2$OAc | H | |
| 483 | 2-Br | H | (CH$_2$)$_n$CH$_2$OAc | H | |
| 484 | H | 4-F | (CH$_2$)$_n$CH$_2$OAc | H | |
| 485 | H | 4-Cl | (CH$_2$)$_n$CH$_2$OAc | H | |
| 486 | H | 4-Br | (CH$_2$)$_n$CH$_2$OAc | H | |
| 487 | 2-F | 4-F | (CH$_2$)$_2$CH$_2$OAc | H | 1-A26 |
| 488 | 2-Cl | 4-Cl | (CH$_2$)$_2$CH$_2$OAc | H | |
| 489 | 2-Br | 4-Br | (CH$_2$)$_2$CH$_2$OAc | H | |
| 490 | 2-F | H | (CH$_2$)$_2$CH$_2$OAc | H | |
| 491 | 2-Cl | H | (CH$_2$)$_2$CH$_2$OAc | H | |
| 492 | 2-Br | H | (CH$_2$)$_2$CH$_2$OAc | H | |
| 493 | H | 4-F | (CH$_2$)$_2$CH$_2$OAc | H | |
| 494 | H | 4-Cl | (CH$_2$)$_2$CH$_2$OAc | H | |
| 495 | H | 4-Br | (CH$_2$)$_2$CH$_2$OAc | H | |
| 496 | 2-F | 4-F | (CH$_2$)$_6$CH$_2$OAc | H | 1-A12 |
| 497 | 2-Cl | 4-Cl | (CH$_2$)$_6$CH$_2$OAc | H | |
| 498 | 2-Br | 4-Br | (CH$_2$)$_6$CH$_2$OAc | H | |
| 499 | 2-F | H | (CH$_2$)$_6$CH$_2$OAc | H | |
| 500 | 2-Cl | H | (CH$_2$)$_6$CH$_2$OAc | H | |
| 501 | 2-Br | H | (CH$_2$)$_6$CH$_2$OAc | H | |
| 502 | H | 4-F | (CH$_2$)$_6$CH$_2$OAc | H | |
| 503 | H | 4-Cl | (CH$_2$)$_6$CH$_2$OAc | H | |
| 504 | H | 4-Br | (CH$_2$)$_6$CH$_2$OAc | H | |
| 505 | 2-F | 4-F | (CH$_2$)$_n$CH$_2$OCOR | H | |
| 506 | 2-Cl | 4-Cl | (CH$_2$)$_n$CH$_2$OCOR | H | |
| 507 | 2-Br | 4-Br | (CH$_2$)$_n$CH$_2$OCOR | H | |
| 508 | 2-F | H | (CH$_2$)$_n$CH$_2$OCOR | H | |
| 509 | 2-Cl | H | (CH$_2$)$_n$CH$_2$OCOR | H | |
| 510 | 2-Br | H | (CH$_2$)$_n$CH$_2$OCOR | H | |
| 511 | H | 4-F | (CH$_2$)$_n$CH$_2$OCOR | H | |
| 512 | H | 4-Cl | (CH$_2$)$_n$CH$_2$OCOR | H | |
| 513 | H | 4-Br | (CH$_2$)$_n$CH$_2$OCOR | H | |
| 514 | 2-F | 4-F | (CH$_2$)$_n$CH$_2$OR | H | |
| 515 | 2-Cl | 4-Cl | (CH$_2$)$_n$CH$_2$OR | H | |
| 516 | 2-Br | 4-Br | (CH$_2$)$_n$CH$_2$OR | H | |
| 517 | 2-F | H | (CH$_2$)$_n$CH$_2$OR | H | |
| 518 | 2-Cl | H | (CH$_2$)$_n$CH$_2$OR | H | |
| 519 | 2-Br | H | (CH$_2$)$_n$CH$_2$OR | H | |
| 520 | H | 4-F | (CH$_2$)$_n$CH$_2$OR | H | |

TABLE 1-continued

Analogues of fluconazole of Formula (1)

| Compound No. | R¹ | R² | R³ | R⁴ | Sample No. |
|---|---|---|---|---|---|
| 521 | H | 4-Cl | $(CH_2)_nCH_2OR$ | H | |
| 522 | H | 4-Br | $(CH_2)_nCH_2OR$ | H | |
| 523 | 2-F | 4-F | $(CH_2)_2CH_2OBn$ | H | 1-A02 |
| 524 | 2-Cl | 4-Cl | $(CH_2)_2CH_2OBn$ | H | |
| 525 | 2-Br | 4-Br | $(CH_2)_2CH_2OBn$ | H | |
| 526 | 2-F | H | $(CH_2)_2CH_2OBn$ | H | |
| 527 | 2-Cl | H | $(CH_2)_2CH_2OBn$ | H | |
| 528 | 2-Br | H | $(CH_2)_2CH_2OBn$ | H | |
| 529 | H | 4-F | $(CH_2)_2CH_2OBn$ | H | |
| 530 | H | 4-Cl | $(CH_2)_2CH_2OBn$ | H | |
| 531 | H | 4-Br | $(CH_2)_2CH_2OBn$ | H | |
| 532 | 2-F | 4-F | $(CH_2)_3CH_2OBn$ | H | 1-A01 |
| 533 | 2-Cl | 4-Cl | $(CH_2)_3CH_2OBn$ | H | |
| 534 | 2-Br | 4-Br | $(CH_2)_3CH_2OBn$ | H | |
| 535 | 2-F | H | $(CH_2)_3CH_2OBn$ | H | |
| 536 | 2-Cl | H | $(CH_2)_3CH_2OBn$ | H | |
| 537 | 2-Br | H | $(CH_2)_3CH_2OBn$ | H | |
| 538 | H | 4-F | $(CH_2)_3CH_2OBn$ | H | |
| 539 | H | 4-Cl | $(CH_2)_3CH_2OBn$ | H | |
| 540 | H | 4-Br | $(CH_2)_3CH_2OBn$ | H | |
| 541 | 2-F | 4-F | $(CH_2)_nCH_2R$ | H | |
| 542 | 2-Cl | 4-Cl | $(CH_2)_nCH_2R$ | H | |
| 543 | 2-Br | 4-Br | $(CH_2)_nCH_2R$ | H | |
| 544 | 2-F | H | $(CH_2)_nCH_2R$ | H | |
| 545 | 2-Cl | H | $(CH_2)_nCH_2R$ | H | |
| 546 | 2-Br | H | $(CH_2)_nCH_2R$ | H | |
| 547 | H | 4-F | $(CH_2)_nCH_2R$ | H | |
| 548 | H | 4-Cl | $(CH_2)_nCH_2R$ | H | |
| 549 | H | 4-Br | $(CH_2)_nCH_2R$ | H | |
| 550 | 2-F | 4-F | $CH_2Ph$ | $(CH_2)_nCH_2R$ | |
| 551 | 2-Cl | 4-Cl | $CH_2Ph$ | $(CH_2)_nCH_2R$ | |
| 552 | 2-Br | 4-Br | $CH_2Ph$ | $(CH_2)_nCH_2R$ | |
| 553 | 2-F | H | $CH_2Ph$ | $(CH_2)_nCH_2R$ | |
| 554 | 2-Cl | H | $CH_2Ph$ | $(CH_2)_nCH_2R$ | |
| 555 | 2-Br | H | $CH_2Ph$ | $(CH_2)_nCH_2R$ | |
| 556 | H | 4-F | $CH_2Ph$ | $(CH_2)_nCH_2R$ | |
| 557 | H | 4-Cl | $CH_2Ph$ | $(CH_2)_nCH_2R$ | |
| 558 | H | 4-Br | $CH_2Ph$ | $(CH_2)_nCH_2R$ | |
| 559 | 2-F | 4-F | $CH_2Ph$ | $CH_3$ | 1-A15 |
| 560 | 2-Cl | 4-Cl | $CH_2Ph$ | $CH_3$ | |
| 561 | 2-Br | 4-Br | $CH_2Ph$ | $CH_3$ | |
| 562 | 2-F | H | $CH_2Ph$ | $CH_3$ | |
| 563 | 2-Cl | H | $CH_2Ph$ | $CH_3$ | |
| 564 | 2-Br | H | $CH_2Ph$ | $CH_3$ | |
| 565 | H | 4-F | $CH_2Ph$ | $CH_3$ | |
| 566 | H | 4-Cl | $CH_2Ph$ | $CH_3$ | |
| 567 | H | 4-Br | $CH_2Ph$ | $CH_3$ | |
| 568 | 2-F | 4-F | H | $(CH_2)_nCH_2Ph$ | |
| 569 | 2-Cl | 4-Cl | H | $(CH_2)_nCH_2Ph$ | |
| 570 | 2-Br | 4-Br | H | $(CH_2)_nCH_2Ph$ | |
| 571 | 2-F | H | H | $(CH_2)_nCH_2Ph$ | |
| 572 | 2-Cl | H | H | $(CH_2)_nCH_2Ph$ | |
| 573 | 2-Br | H | H | $(CH_2)_nCH_2Ph$ | |
| 574 | H | 4-F | H | $(CH_2)_nCH_2Ph$ | |
| 575 | H | 4-Cl | H | $(CH_2)_nCH_2Ph$ | |
| 576 | H | 4-Br | H | $(CH_2)_nCH_2Ph$ | |
| 577 | 2-F | 4-F | H | $CH_2CH_2Ph$ | 1-A14 |
| 578 | 2-Cl | 4-Cl | H | $CH_2CH_2Ph$ | |
| 579 | 2-Br | 4-Br | H | $CH_2CH_2Ph$ | |
| 580 | 2-F | H | H | $CH_2CH_2Ph$ | |
| 581 | 2-Cl | H | H | $CH_2CH_2Ph$ | |
| 582 | 2-Br | H | H | $CH_2CH_2Ph$ | |
| 583 | H | 4-F | H | $CH_2CH_2Ph$ | |
| 584 | H | 4-Cl | H | $CH_2CH_2Ph$ | |
| 585 | H | 4-Br | H | $CH_2CH_2Ph$ | |
| 586 | 2-F | 4-F | $(CH_2)_nCH_2OCOCH_2NHBoc$ | H | |
| 587 | 2-Cl | 4-Cl | $(CH_2)_nCH_2OCOCH_2NHBoc$ | H | |
| 588 | 2-Br | 4-Br | $(CH_2)_nCH_2OCOCH_2NHBoc$ | H | |
| 589 | 2-F | H | $(CH_2)_nCH_2OCOCH_2NHBoc$ | H | |
| 590 | 2-Cl | H | $(CH_2)_nCH_2OCOCH_2NHBoc$ | H | |
| 591 | 2-Br | H | $(CH_2)_nCH_2OCOCH_2NHBoc$ | H | |
| 592 | H | 4-F | $(CH_2)_nCH_2OCOCH_2NHBoc$ | H | |
| 593 | H | 4-Cl | $(CH_2)_nCH_2OCOCH_2NHBoc$ | H | |
| 594 | H | 4-Br | $(CH_2)_nCH_2OCOCH_2NHBoc$ | H | |
| 595 | 2-F | 4-F | $(CH_2)_3CH_2OCOCH_2NHBoc$ | H | 1-A24 |

TABLE 1-continued

Analogues of fluconazole of Formula (1)

| Compound No. | R¹ | R² | R³ | R⁴ | Sample No. |
|---|---|---|---|---|---|
| 596 | 2-Cl | 4-Cl | $(CH_2)_3CH_2OCOCH_2NHBoc$ | H | |
| 597 | 2-Br | 4-Br | $(CH_2)_3CH_2OCOCH_2NHBoc$ | H | |
| 598 | 2-F | H | $(CH_2)_3CH_2OCOCH_2NHBoc$ | H | |
| 599 | 2-Cl | H | $(CH_2)_3CH_2OCOCH_2NHBoc$ | H | |
| 600 | 2-Br | H | $(CH_2)_3CH_2OCOCH_2NHBoc$ | H | |
| 601 | H | 4-F | $(CH_2)_3CH_2OCOCH_2NHBoc$ | H | |
| 602 | H | 4-Cl | $(CH_2)_3CH_2OCOCH_2NHBoc$ | H | |
| 603 | H | 4-Br | $(CH_2)_3CH_2OCOCH_2NHBoc$ | H | |
| 604 | 2-F | 4-F | $(CH_2)_nCH_2OCOCH_2NHR$ | H | |
| 605 | 2-Cl | 4-Cl | $(CH_2)_nCH_2OCOCH_2NHR$ | H | |
| 606 | 2-Br | 4-Br | $(CH_2)_nCH_2OCOCH_2NHR$ | H | |
| 607 | 2-F | H | $(CH_2)_nCH_2OCOCH_2NHR$ | H | |
| 608 | 2-Cl | H | $(CH_2)_nCH_2OCOCH_2NHR$ | H | |
| 609 | 2-Br | H | $(CH_2)_nCH_2OCOCH_2NHR$ | H | |
| 610 | H | 4-F | $(CH_2)_nCH_2OCOCH_2NHR$ | H | |
| 611 | H | 4-Cl | $(CH_2)_nCH_2OCOCH_2NHR$ | H | |
| 612 | H | 4-Br | $(CH_2)_nCH_2OCOCH_2NHR$ | H | |
| 613 | 2-F | 4-F | $(CH_2)_3CH_2OCOCH_2NH_2$ | H | 1-A25 |
| 614 | 2-Cl | 4-Cl | $(CH_2)_3CH_2OCOCH_2NH_2$ | H | |
| 615 | 2-Br | 4-Br | $(CH_2)_3CH_2OCOCH_2NH_2$ | H | |
| 616 | 2-F | H | $(CH_2)_3CH_2OCOCH_2NH_2$ | H | |
| 617 | 2-Cl | H | $(CH_2)_3CH_2OCOCH_2NH_2$ | H | |
| 618 | 2-Br | H | $(CH_2)_3CH_2OCOCH_2NH_2$ | H | |
| 619 | H | 4-F | $(CH_2)_3CH_2OCOCH_2NH_2$ | H | |
| 620 | H | 4-Cl | $(CH_2)_3CH_2OCOCH_2NH_2$ | H | |
| 621 | H | 4-Br | $(CH_2)_3CH_2OCOCH_2NH_2$ | H | |
| 622 | 2-F | 4-F | $(CH_2)_nCH_3$ | $(CH_2)_nCH_3$ | |
| 623 | 2-Cl | 4-Cl | $(CH_2)_nCH_3$ | $(CH_2)_nCH_3$ | |
| 624 | 2-Br | 4-Br | $(CH_2)_nCH_3$ | $(CH_2)_nCH_3$ | |
| 625 | 2-F | H | $(CH_2)_nCH_3$ | $(CH_2)_nCH_3$ | |
| 626 | 2-Cl | H | $(CH_2)_nCH_3$ | $(CH_2)_nCH_3$ | |
| 627 | 2-Br | H | $(CH_2)_nCH_3$ | $(CH_2)_nCH_3$ | |
| 628 | H | 4-F | $(CH_2)_nCH_3$ | $(CH_2)_nCH_3$ | |
| 629 | H | 4-Cl | $(CH_2)_nCH_3$ | $(CH_2)_nCH_3$ | |
| 630 | H | 4-Br | $(CH_2)_nCH_3$ | $(CH_2)_nCH_3$ | |
| 631 | 2-F | 4-F | $(CH_2)_2CH_3$ | $(CH_2)_3CH_3$ | 1-A05 |
| 632 | 2-Cl | 4-Cl | $(CH_2)_2CH_3$ | $(CH_2)_3CH_3$ | |
| 633 | 2-Br | 4-Br | $(CH_2)_2CH_3$ | $(CH_2)_3CH_3$ | |
| 634 | 2-F | H | $(CH_2)_2CH_3$ | $(CH_2)_3CH_3$ | |
| 635 | 2-Cl | H | $(CH_2)_2CH_3$ | $(CH_2)_3CH_3$ | |
| 636 | 2-Br | H | $(CH_2)_2CH_3$ | $(CH_2)_3CH_3$ | |
| 637 | H | 4-F | $(CH_2)_2CH_3$ | $(CH_2)_3CH_3$ | |
| 638 | H | 4-Cl | $(CH_2)_2CH_3$ | $(CH_2)_3CH_3$ | |
| 639 | H | 4-Br | $(CH_2)_2CH_3$ | $(CH_2)_3CH_3$ | |

Example 5

General Method of Preparation of Compounds of Formula 4

A mixture of compound of Formula (3) (1 mmol), ammonium acetate (1-10 mmol) and formamide (10-20 mmol) was stirred under reflux for 2 to 20 hrs, cooled, diluted with water, extracted with ethyl acetate, dried, concentrated and purified by column chromatography to obtain the compound of the Formula (4).

The following compounds were prepared by the method described above:

1) 6-(4-Benzyloxypropyl)-thieno[2,3-d]pyrimidin-4 (3H)-one (4-A02)

A mixture of ethyl 2-amino-5-(3-benzyloxypropyl)-thiophene-3-carboxylate of Formula (3-A02): (5.5 g, 0.017 mole), ammonium acetate (10.6 g, 0.14 mole) and formamide (17.12 ml, 0.43 mole), was stirred under reflux at 145° C. for 12 hours. It was then cooled, diluted with water (50 ml), extracted with ethyl acetate (3×30 ml), dried, concentrated and purified by column chromatography to obtain the pure 6-(4-Benzyloxypropyl)-thieno[2,3-d]pyrimidin-4(3H)-one of Formula (4-A02) (4.5 gm, 87.2%).

1HNMR (CDCl3, 200 MHz): 1.91-2.12 (m, 2H), 3.01 (t, J=6 Hz, 2H), 3.53 (t, J=6 Hz, 2H), 4.51 (s, 2H), 7.17 (s, 1H), 7.33 (bs, 5H), 8.03 (s, 1H), 12.84 (bs, 1H).

2) 6-(3-Acetoxypropyl)-thieno[2,3-d]pyrimidin-4 (3H)-one (4-A26)

A mixture of ethyl 2-amino-5-(3-acetyloxypropyl)-thiophene-3-carboxylate (2.6 g, 9.7 mmole), ammonium acetate (0.74 g, 9.7 mmole) and formamide (8.64 ml, 19.2 mmole), was stirred under reflux at 145° C. for 12 hours. It was then cooled, diluted with water (20 ml), extracted with ethyl acetate (3×25 ml), dried, concentrated and purified by column chromatography to obtain the pure 6-(3-Acetoxypropyl)-thieno[2,3-d]pyrimidin-4(3H)-one of Formula (4-A26) (1.8 gm, 75%).

1HNMR (CDCl3, 200 MHz): 1.94-2.18 (m including s at 2.07, 5H), 2.85-3.08 (m, 2H), 4.05-4.30 (m, 2H), 7.18 (s, 1H), 8.03 (s, 1H), 12.63 (bs, 1H).

3) 5,6,7,8-Tetrahydrobenzothieno[2,3-d]pyrimidin-4(3H)-one (4-A09)

A mixture of ethyl 2-amino-4,5,6,7-tetrahydrobenzo[b]thiophene-3-carboxylate (0.7 g, 3.1 mmole), ammonium acetate (0.31 g, 4.04 mmole) and formamide (0.67 ml, 16.8 mmole), was stirred under reflux at 140° C. for 13 hours. It was then cooled, diluted with water (20 ml), extracted with ethyl acetate (3×35 ml), dried, concentrated and purified by column chromatography to obtain the pure 5,6,7,8-tetrahydrobenzothieno[2,3-d]pyrimidin-4(3H)-one of Formula (4-A09) (0.53 gm, 82%).

1HNMR (CDCl3+DMSO-d6, 200 MHz): 1.36-1.52 (m, 4H), 2.31-2.40 (m, 2H), 2.51-2.62 (m, 2H), 7.45 (s, 1H).

4) 6-(4-Benzyloxybutyl)-thieno[2,3-d]pyrimidin-4(3H)-one (4-A01)

1HNMR (CDCl3, 200 MHz): 1.61-1.92 (m, 4H), 2.89 (t, J=6 Hz, 2H), 3.51 (t, J=6 Hz, 2H), 4.51 (s, 2H), 7.17 (s, 1H), 7.34 (bs, 5H), 8.02 (s, 1H), 12.54 (bs, 1H).

5) 6-(n-Hexyl)-thieno[2,3-d]pyrimidin-4(3H)-one (4-A03)

1HNMR (CDCl3, 200 MHz): 0.90 (t, J=6 Hz, 3H), 1.21-1.50 (m, 6H), 1.61-1.86 (m, 2H), 2.87 (t, J=8 Hz, 2H), 7.15 (s, 1H), 8.03 (s, 1H), 12.80 (bs, 1H).

6) 6-(n-Pentyl)-thieno[2,3-d]pyrimidin-4(3I)-one (4-A04)

1HNMR (CDCl3, 200 MHz): 0.89 (t, J=6 Hz, 3H), 1.16-1.45 (m, 4H), 1.52-1.83 (m, 2H), 2.84 (t, J=8 Hz, 2H), 7.13 (s, 1H), 8.07 (s, 1H), 12.90 (bs, 1H).

7) 5-n-Butyl-6-(n-propyl)-thieno[2,3-d]pyrimidin-4(3H)-one (4-A05)

1HNMR (CDCl3, 200 MHz): 0.93 (t, J=6 Hz, 3H), 0.99 (t, J=6 Hz, 3H), 1.26-1.85 (m, 6H), 2.79 (t, J=6 Hz, 2H), 2.95 (t, J=6 Hz, 2H), 7.95 (s, 1H), 12.34 (bs, 1H).

8) 6-(n-Heptyl)-thieno[2,3-d]pyrimidin-4(3H)-one (4-A06)

1HNMR (CDCl3, 200 MHz): 0.89 (t, J=6 Hz, 3H), 1.26-1.38 (m, 8H), 1.60-1.78 (m, 2H), 2.87 (t, J=6 Hz, 2H), 7.17 (s, 1H), 8.05 (s, 1H), 12.82 (bs, 1H).

9) 3,5,6,7-Tetrahydrocyclopenta[4,5]thieno[2,3-d]pyrimidin-4(3H)-one (4-A07)

The crude compound obtained was used as such for further reaction.

10) 6-Methyl-5-n-pentyl-thieno[2,3-d]pyrimidin-4(3H)-one (4-A08)

1HNMR (CDCl3, 200 MHz): 0.91 (bt, J=6 Hz, 3H), 1.25-1.50 (m, 4H), 1.52-1.68 (m, 2H), 2.43 (s, 3H), 2.93 (t, J=8 Hz, 2H), 7.96 (s, 1H), 12.32 (bs, 1H).

11) 6-n Hexyl-5-methyl-thieno[2,3-d]pyrimidin-4(3H)-one (4-A10)

1HNMR (CDCl3, 200 MHz): 0.90 (t, J=6 Hz, 3H), 1.22-1.46 (m, 6H), 1.52-1.76 (m, 2H), 2.52 (s, 3H), 2.78 (t, J=6 Hz, 2H), 7.96 (s, 1H), 12.32 (bs, 1H).

11) 5-Methyl-6-n-pentyl-thieno[2,3-d]pyrimidin-4(3H)-one (4-A11)

1HNMR (CDCl3, 200 MHz): 0.91 (t, J=6 Hz, 3H), 1.25-1.48 (m, 4H), 1.55-1.75 (m, 2H), 2.52 (s, 3H), 2.79 (t, J=8 Hz, 2H), 8.20 (s, 1H).

12) 6-(7-Acetoxyheptyl)-thieno[2,3-d]pyrimidin-4(3H)-one (4-A12)

1HNMR (CDCl3, 200 MHz): 1.24-1.42 (m, 6H), 1.48-1.77 (m, 4H), 1.97 (s, 3H), 2.79 (t, J=8 Hz, 2H), 3.98 (t, J=7 Hz, 2H), 7.08 (s, 1H), 8.03 (s, 1H).

13) 5-(2-Phenylethyl)-thieno[2,3-d]pyrimidin-4(3H)-one (4-A14)

1HNMR (CDCl3+DMSO-d6, 200 MHz): 3.05 (t, J=7 Hz, 2H), 3.34 (t, J=7 Hz, 2H), 6.84 (s, 1H), 7.30 (bs, 5H), 8.00 (s, 1H).

14) 6-Benzyl-5-methyl-thieno[2,3-d]pyrimidin-4(3H)-one (4-A15)

1HNMR (DMSOd6, 200 MHz):: 2.48 (s, 3H), 4.13 (s, 2H), 7.22-7.34 (m, 5H), 8.00 (s, 1H).

15) 6-(n-Decyl)-thieno[2,3-d]pyrimidin-4(3H)-one (4-A16)

1HNMR (CDCl3, 200 MHz): 0.88 (t, J=6 Hz, 3H), 1.18-1.42 (m, 14H), 1.62-1.83 (m, 2H), 2.86 (t, J=6 Hz, 2H), 7.17 (s, 1H), 8.15 (s, 1H).

16) 6-(n-Nonyl)-thieno[2,3-d]pyrimidin-4(3H)-one (4-A17)

1HNMR (CDCl3, 200 MHz): 0.91 (t, J=6 Hz, 3H), 1.14-1.55 (m, 12H), 1.65-1.92 (m, 2H), 2.89 (t, J=6 Hz, 2H), 7.19 (s, 1H), 8.09 (s, 1H), 12.96 (bs, 1H).

17) 6-(n-Propyl)-thieno[2,3-d]pyrimidin-4(3H)-one (4-A18)

1HNMR (CDCl3, 200 MHz): 1.01 (t, J=6 Hz, 3H), 1.67-1.85 (m, 2H), 2.84 (t, J=6 Hz, 2H), 7.16 (s, 1H), 8.05 (s, 1H), 12.74 (bs, 1H).

18) 7,8,9,10,11,12,13,14,15,16-Decahydrocyclododeca[4,5]thieno[2,3-d]pyrimidin-4(3H)-one (4-A19)

1HNMR (CDCl3, 200 MHz): 1.21-1.58 (m, 12H), 1.68-2.01 (m, 4H), 2.79-2.99 (m, 4H), 7.98 (s, 1H), 12.08 (bs, 1H).

19) 5-Methyl-6-n-octyl-thieno[2,3-d]pyrimidin-4 (3H)-one (4-A20)

1HNMR (CDCl3, 200 MHz): 0.92 (t, J=7 Hz, 3H), 1.20-1.52 (m, 10H), 1.60-1.75 (m, 2H), 2.55 (s, 3H), 2.82 (t, J=8 Hz, 2H), 8.19 (s, 1H).

20) 6-n-Butyl-5-methyl-thieno[2,3-d]pyrimidin-4 (3H)-one (4-A21)

1HNMR (CDCl3, 200 MHz): 0.96 (t, J=6 Hz, 3H), 1.32-1.73 (m, 4H), 2.52 (s, 3H), 2.79 (t, J=8 Hz, 2H), 7.99 (s, 1H), 12.48 (bs, 1H).

21) 6-Ethyl-thieno[2,3-d]pyrimidin-4(3H)-one (4-A22)

1HNMR (CDCl3, 200 MHz): 1.39 (t, J=8 Hz, 3H), 2.92 (q, J=8 Hz, 2H), 7.17 (s, 1H), 8.02 (s, 1H).

Example 6

General Methods of Preparation of Compounds of Formula (3)

Method A:
A mixture of ethyl cyanoacetate (1 eq), sulphur (1 eq), triethyl amine (0.5 eq) and a ketone or aldehyde (1 eq) was stirred at 30 to 80° C. for 8 to 20 hrs, cooled, diluted with water, extracted with ethyl acetate, dried, concentrated and purified by column chromatography to obtain the pure compounds of the Formula (3).

Method B:
A mixture of ethyl cyanoacetate (1 eq), sulphur (1 eq), morpholine (1 eq) and ketone or aldehyde (1 eq) in ethanol was stirred at 30 to 60° C. for 5 to 20 hrs, ethanol was removed on rotavapor, the reaction mixture was extracted with ethyl acetate, dried, concentrated and purified by column chromatography to get the pure compounds of the Formula (3).

1. Ethyl 2-amino-5-(3-benzyloxypropyl)-thiophene-3-carboxylate (3-A02)

A mixture of ethyl cyanoacetate (2.77 ml, 26 mmol), sulphur (0.83 g, 26 mmol), triethyl amine (1.82 ml, 13 mmol) and 5-benzyloxy-1-pentanal (5.00 g, 26 mmol) in DMF (40 ml) was stirred at 45-50° C. for 12 hours. It was then cooled, diluted with water (100 ml), extracted with ethyl acetate (2×100 ml), dried, concentrated and purified by column chromatography to obtain the pure ethyl 2-amino-5-(3-benzyloxypropyl)-thiophene-3-carboxylate (4.5 gm, 54%).

$^1$HNMR (CDCl$_3$, 200 MHz): 1.34 (t, J=8 Hz, 3H), 1.80-1.96 (m, 2H), 2.70 (t, J=7 Hz, 2H), 3.51 (t, J=7 Hz, 2H), 4.25 (q, J=7 Hz, 2H), 4.51 (s, 2H), 5.80 (bs, 2H), 6.64 (s, 1H), 7.34 (bs, 5H).

2. Ethyl 2-amino-4,5,6,7-tetrahydrobenzo[b] thiophene-3-carboxylate (3-A09)

A mixture of ethyl cyanoacetate (1.15 g, 0.01 mol), sulphur (0.32 g, 0.01 mol), triethyl amine (0.52 g, 0.005 mol) and cyclohexanone (1.0 g, 0.01 mol) in DMF (10 ml) was stirred at 55° C. for 12 hours. It was cooled, diluted with water (80 ml), extracted with ethyl acetate (2×100 ml), dried, concentrated and purified by column chromatography to obtain the pure ethyl 2-amino-4,5,6,7-tetrahydrobenzo[b]thiophene-3-carboxylate of Formula (3-A09) (1.13 gm, 50%).

1HNMR (CDCl3, 200 MHz): 1.27 (t, J=7 Hz, 3H), 1.62-1.78 (m, 4H), 2.35-2.50 (m, 2H), 2.54-2.70 (m, 2H), 4.19 (q, J=7 Hz, 2H).

3. Ethyl 5-(3-acetoxypropyl)-2-aminothiophene-3-carboxylate (3-A26)

A mixture of ethyl cyanoacetate (6.2 ml, 50 mmol), sulphur (4.6 g, 50 mmol), morpholine (4.3 ml, 50 mmol) and 5-acetoxy-1-pentanal (8 g, 50 mmol) in ethanol (25 ml) was stirred at 80° C. for 12 hours. Ethanol was removed on rotavapor, the reaction mixture was diluted with water (100 ml), extracted with ethyl acetate (3×100 ml), dried, concentrated and purified by column chromatography to get the pure ethyl 5-(3-acetoxypropyl)-2-amino-thiophene-3-carboxylate (6.4 gm, 42.5%).

1HNMR (CDCl3, 200 MHz): 1.32 (t, J=7 Hz, 2H), 1.81-1.98 (m, 2H), 2.05 (s, 3H), 2.65 (t, J=7 Hz, 2H), 4.08 (t, J=7 Hz, 2H), 4.24 (q, J=7 Hz, 2H), 5.18 (bs, 2H), 6.64 (s, 1H).

The methods described above were used for preparing more compounds some of which are given below:

4. Ethyl 2-amino-5-(4-benzyloxybutyl)-thiophene-3-carboxylate (3-A01)

1HNMR (CDCl3, 200 MHz): 1.33 (t, J=8 Hz, 3H), 1.60-1.75 (m, 4H), 2.59 (bt, J=6 Hz, 2H), 3.48 (bt, J=6 Hz, 2H), 4.25 (q, J=8 Hz, 2H), 4.50 (s, 2H), 5.77 (bs, 2H), 6.62 (s, 1H), 7.33 (bs, 5H).

5. Ethyl 2-amino-5-n-hexyl-thiophene-3-carboxylate (3-A03)

1HNMR (CDCl3, 200 MHz): 0.90 (bt, J=6 Hz, 3H), 1.22-1.42 (m, 9H), 1.49-1.63 (m, 2H), 2.57 (t, J=7 Hz, 2H), 4.26 (q, J=7 Hz, 2H), 5.79 (bs, 2H), 6.61 (s, 1H).

6. Ethyl 2-amino-5-n-pentyl-thiophene-3-carboxylate (3-A04)

1HNMR (CDCl3, 200 MHz): 0.88 (bt, J=6 Hz, 3H), 1.21-1.40 (m, 7H), 1.49-1.71 (m, 2H), 2.55 (t, J=8 Hz, 2H), 4.24 (q, J=7 Hz, 2H), 5.65 (bs, 2H), 6.61 (s, 1H).

7. Ethyl 2-amino-5-n-heptyl-thiophene-3-carboxylate (3-A06)

1HNMR (CDCl3, 200 MHz): 0.89 (bt, J=6 Hz, 3H), 1.26-1.48 (m, 11H), 1.51-1.71 (m, 2H), 2.58 (t, J=8 Hz, 2H), 4.26 (q, J=7 Hz, 2H), 5.49 (bs, 2H), 6.63 (s, 1H).

8. Ethyl 2-amino-5,6-dihydro-4H-cyclopenta[b] thiophene-3-carboxylate (3-A07)

1HNMR (CDCl3, 200 MHz): 1.32 (t, J=7 Hz, 3H), 2.22-2.38 (m, 2H), 2.65-2.90 (m, 4H), 4.24 (q, J=7 Hz, 2H), 5.85 (bs, 2H).

9. Ethyl 2-amino-5-methyl-4-(n-pentyl)-thiophene-3-carboxylate (3-A08)

1HNMR (CDCl3, 200 MHz): 0.91 (t, J=6 Hz, 3H), 1.30-1.52 (m, 7H), 2.16 (s, 3H), 2.35-2.50 (m, 2H), 2.55-2.70 (m, 2H), 4.29 (q, J=7 Hz, 2H), 5.92 (bs, 2H).

10. Ethyl 2-amino-5-n-hexyl-4-methyl-thiophene-3-carboxylate (3-A10)

1HNMR (CDCl3, 200 MHz): 0.90 (bt, J=6 Hz, 3H), 1.22-1.40 (m, 9H), 1.45-1.63 (m, 2H), 2.18 (s, 3H), 2.54 (t, J=8 Hz, 2H), 4.28 (q, J=8 Hz, 2H), 5.01 (bs, 2H).

11. Ethyl 2-amino-5(7-acetoxy-n-heptyl)-thiophene-3-carboxylate (3-A12)

1HNMR (CDCl3, 200 MHz): 1.21-1.40 (m, 9H), 1.45-1.67 (m, 4H), 2.00 (s, 3H), 2.52 (t, J=8 Hz, 2H), 4.00 (t, J=6 Hz, 2H), 4.20 (q, J=8 Hz, 2H), 5.67 (bs, 2H), 6.57 (s, 1H).

12. Ethyl 2-amino-5-(2-phenylethyl)-thiophene-3-carboxylate (3-A14)

1HNMR (CDCl3, 200 MHz): 1.35 (t, J=8 Hz, 3H), 2.74-3.07 (m, 4H), 4.32 (q, J=8 Hz, 2H), 5.19 (bs, 2H), 7.15-7.26 (m, 6H).

13. Ethyl 2-amino-5-benzyl-4-methyl-thiophene-3-carboxylate (3-A15)

1HNMR (CDCl3, 200 MHz): 1.35 (t, J=8 Hz, 3H), 2.25 (s, 3H), 3.90 (s, 2H), 4.29 (q, J=7 Hz, 2H), 5.18 (bs, 2H), 7.19 (bs, 5H).

14. Ethyl 2-amino-5-n-decyl-thiophene-3-carboxylate (3-A16)

1HNMR (CDCl3, 200 MHz): 0.88 (bt, J=6 Hz, 3H), 1.18-1.40 (m including t at 1.33 with J=7 Hz, 17H), 1.49-1.65 (m, 2H), 2.56 (t, J=7 Hz, 2H), 4.25 (q, J=7 Hz, 2H), 5.40 (bs, 2H), 6.63 (s, 1H).

15. Ethyl 2-amino-5-n-nonyl-thiophene-3-carboxylate (3-A17)

1HNMR (CDCl3, 200 MHz): 0.88 (bt, J=7 Hz, 3H), 1.15-1.42 (m including t at 1.32 with J=7 Hz, 15H), 1.47-1.65 (m, 2H), 2.54 (t, J=7 Hz, 2H), 4.24 (q, J=7 Hz, 2H), 5.78 (bs, 2H), 6.61 (s, 1H).

16. Ethyl 2-amino-5-n-propyl-thiophene-3-carboxylate (3-A18)

1HNMR (CDCl3, 200 MHz): 0.95 (t, J=7 Hz, 3H), 1.34 (t, J=7 Hz, 3H), 1.51-1.71 (m, 2H), 2.56 (t, J=7 Hz, 2H), 4.26 (q, J=7 Hz, 2H), 4.75 (bs, 2H), 6.64 (s, 1H).

17. Ethyl 2-amino-4,5,6,7,8,9,10,11,12,13-decahydro-[1]cyclododeca[b]thiophene-3-carboxylate (3-A19)

1HNMR (CDCl3, 200 MHz): 1.21-1.50 (m, 15H), 1.55-1.71 (m, 4H), 2.54-2.71 (m, 4H), 4.27 (q, J=7 Hz, 2H).

18. Ethyl 2-amino-5-ethyl-thiophene-3-carboxylate (3-A22)

1HNMR (CDCl3, 200 MHz): 1.23 (t, J=7 Hz, 3H), 1.34 (t, J=7 Hz, 3H), 2.62 (q, J=7 Hz, 2H), 4.26 (q, J=7 Hz, 2H), 4.62 (bs, 2H), 6.64 (s, 1H).

Example 7

Antifungal Activity Testing

The compounds of Formula 1 are antifungal agents effective against *Candida albicans*. In vitro evaluation of antifungal activity was performed by determining the minimum inhibitory concentration (MIC). Anti-fungal susceptibility testing of these anti-fungal compounds was done by broth dilution method using RPMI 1640 medium with MOPS buffer. Known anti-fungal agents like fluconazole and amphotericin-B were used as positive control. End points were determined after 48 hours visually and by using spectrophotometer wherever necessary. Different dilutions were tried and various sets of experiments performed. The activity parameters are enumerated in Table 1:

TABLE 1

MIC obtained by broth macro-dilution method

| | | | MIC against fungi in µg/ml | | |
|---|---|---|---|---|---|
| No. | Code no. | Structure R1 = R2 = 2,4-difluoro | C. albicans (ATCC 24433) | A. niger (ATCC 16404) | F. proliferatum (ATCC 10052) |
| | Fluconazole | | 0.25-1 | 64-128 | >128 |
| | Amphotericin B | | 0.12-0.25 | 0.25-1 | 1-2 |
| 01 | 1-A01 | R3 = —(CH$_2$)$_4$OBn, R4 = H | 0.06-0.12 | NI till 4 | NI till 4 |
| 02 | 1-A02 | R3 = —(CH$_2$)$_3$OBn, R4 = H | 0.06-0.12 | NI till 4 | NI till 4 |
| 03 | 1-A03 | R3 = —(CH$_2$)$_5$Me, R4 = H | 0.03-0.06 | NI till 2 | NI till 2 |
| 04 | 1-A04 | R3 = —(CH$_2$)$_4$Me, R4 = H | 0.03-0.06 | NI till 4 | NI till 4 |
| 05 | 1-A05 | R3 = —(CH$_2$)$_2$Me, R4 = —(CH$_2$)$_3$Me | 2-4 | NI till 4 | NI till 4 |
| 06 | 1-A06 | R3 = —(CH$_2$)$_6$Me, R4 = H | 0.06-0.12 | NI till 2 | NI till 2 |
| 07 | 1-A07 | R3, R4 = —(CH$_2$)$_3$— | 0.25-0.5 | NI till 2 | NI till 2 |
| 08 | 1-A08 | R3 = —Me, R4 = —(CH$_2$)$_4$Me | 2-4 | NI till 4 | NI till 4 |
| 09 | 1-A09 | R3, R4 = —(CH$_2$)$_4$— | 0.25-0.5 | NI till 8 | NI till 8 |
| 10 | 1-A10 | R3 = —(CH$_2$)$_5$Me, R4 = —Me | 1-2 | NI till 2 | NI till 2 |
| 11 | 1-A11 | R3 = —(CH$_2$)$_4$Me, R4 = —Me | 1-2 | NI till 2 | NI till 2 |
| 12 | 1-A12 | R3 = —(CH$_2$)$_7$OAc, R4 = H | 0.12-0.25 | NI till 2 | NI till 2 |
| 13 | 1-A13 | R3 = —(CH$_2$)$_7$OH, R4 = H | 0.12-0.25 | NI till 16 | NI till 16 |
| 14 | 1-A14 | R3 = H, R4 = (CH$_2$)$_2$Ph | 0.5-1 | NI till 2 | NI till 2 |
| 15 | 1-A15 | R3 = CH$_2$Ph, R4 = CH$_3$ | 1-2 | NI till 4 | NI till 4 |
| 16 | 1-A16 | R3 = (CH$_2$)$_9$CH$_3$, R4 = H | 1-2 | NI till 2 | NI till 2 |

TABLE 1-continued

MIC obtained by broth macro-dilution method

| | | Structure | MIC against fungi in μg/ml | | |
|---|---|---|---|---|---|
| No. | Code no. | R1 = R2 = 2,4-difluoro | C. albicans (ATCC 24433) | A. niger (ATCC 16404) | F. proliferatum (ATCC 10052) |
| 17 | 1-A17 | R3 = (CH$_2$)$_8$CH$_5$, R4 = H | 0.25-0.5 | NI till 4 | NI till 4 |
| 18 | 1-A18 | R3 = (CH$_2$)$_2$CH$_5$, R4 = H | 0.06-0.12 | NI till 32 | NI till 32 |
| 19 | 1-A19 | R3, R4 = (CH$_2$)$_{10}$ | NI till 2 | NI till 2 | NI till 2 |
| 20 | 1-A22 | R3 = CH$_2$CH$_3$, R4 = H | 0.06-0.12 | NI till 16 | NI till 16 |
| 21 | 1-A23 | R3 = —(CH$_2$)$_4$OH R4 = H | 1-2 | NI till 64 | NI till 64 |
| 22 | 1-A24 | R3 = —(CH$_2$)$_4$OCOCH$_2$—NHBoc, R4 = H | 0.5-1 | NI till 16 | NI till 16 |
| 23 | 1-A25 | R3 = —(CH$_2$)$_4$OCOCH$_2$NH$_2$, R4 = H | 4-8 | NI till 8 | NI till 8 |
| 24 | 1-A26 | R3 = —(CH$_2$)$_3$OAc, R4 = H | 1-2 | NI till 64 | NI till 64 |
| 25 | 1-A27 | R3 = —(CH$_2$)$_3$OH R4 = H | 2-4 | NI till 128 | NI till 128 |
| 26 | 1-A28 | R3 = CH$_3$ R4 = H | 0.25-0.5 | NI till 64 | NI till 64 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. An antifungal compound, comprising:
a compound of the Formula (1):

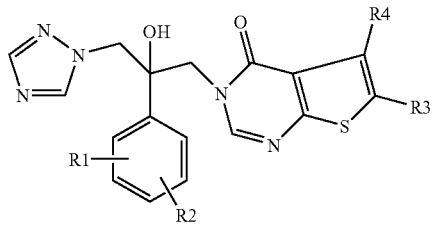

Formula 1 wherein,
R1 is hydrogen or a halogen selected from fluorine, chlorine, bromine or iodine;
R2 is hydrogen or a halogen selected from fluorine, chlorine, bromine or iodine; and either
a) R3 and R4, which may be the same or different, each represents a hydrogen, alkyl group of linear or branched chain of 1 to 20 carbon atoms optionally substituted with aryl group, hydroxyl group, alkanoate group, amino acetyloxy group, N-Boc-amino acetyloxy group, alkoxy (—OR) group (wherein R=alkyl group with 1 to 4 carbon atoms), benzyloxy, arylalkyl group (wherein the aryl group is phenyl which is either unsubstituted or substituted with alkyl group of 1 to 3 carbon atoms), or cycloalkyl group with 3 to 10 carbon atoms; or
R3 and R4 together form an alkylene chain having between 3 and 10 carbon atoms;
a stereochemically isomeric form thereof; or
a pharmaceutically acceptable salt thereof.

2. A process of preparing an antifungal compound of Formula (1), comprising:

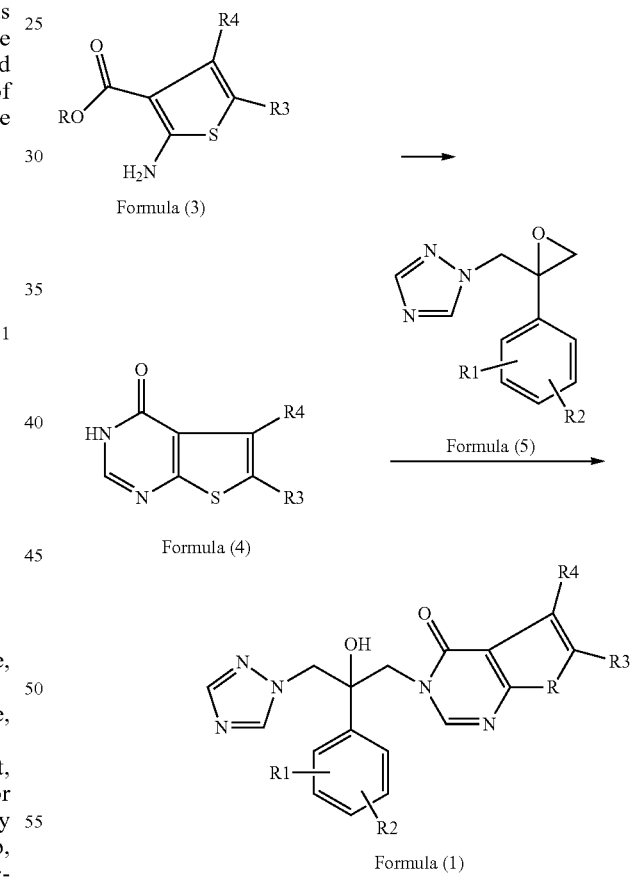

Scheme (1)

a) preparing a 2-amino-4 and/or 5-substituted thiophene-3-carboxylate of Formula (3) by Gewald synthesis, wherein:
R is methyl or ethyl, and either
i) R3 and R4, which may be the same or different, each represent a hydrogen, alkyl group of linear or branched chain of 1 to 20 carbon atoms optionally substituted with aryl group, hydroxyl group, alkanoate group, amino acetyloxy group, N-Bocamino acetyloxy group, alkoxy (—OR) group (wherein R=alkyl group with 1 to 4 carbon atoms), benzyloxy, arylalkyl group (wherein the aryl group is phenyl which is either unsubstituted or substituted with alkyl group of 1 to 3 carbon atoms), or cycloalkyl group with 3 to 10 carbon atoms); or ii) R3 and R4 together form an alkylene chain having between 3 and 10 carbon atoms;

b) contacting said 2-amino-4 and/or 5-substituted thiophene-3-carboxylate of Formula (3) with formamide and ammonium acetate to obtain the thieno-[2,3-d]-pyrimidin-4(3H)-one of Formula (4), wherein R3 and R4 are as defined above; and c) treating the compound of Formula (4) with an epoxide of Formula (5) in the presence of a base to obtain an antifungal compound of the Formula (1), wherein:

R1 and R2 are each hydrogen or a halogen selected from fluorine, chlorine, bromine or iodine.

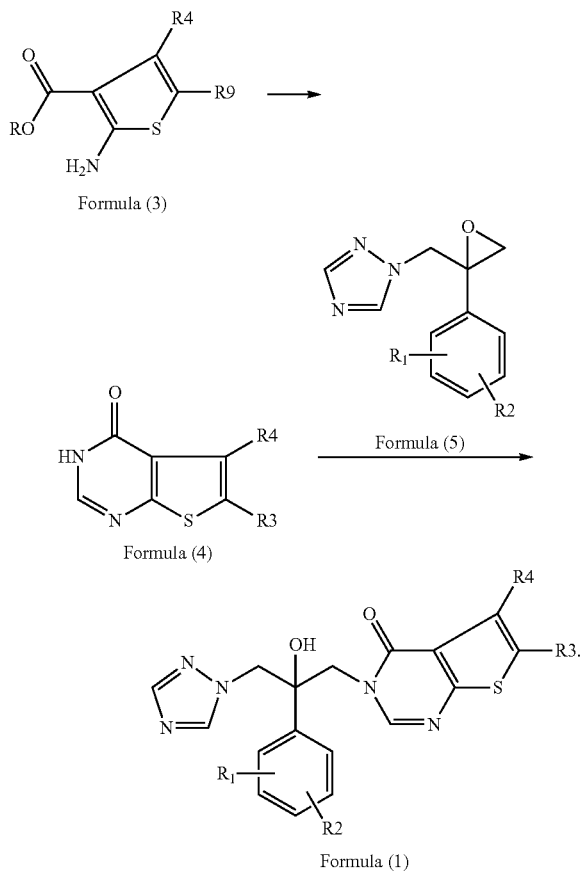

3. A compound according to claim 1 selected from the group consisting of:

6-(4-Benzyloxybutyl)-3-[2-(2,4-difluorophenyl)-2-hydroxy-3-[1,2,4]triazol-1-ylpropyl]-thieno[2,3-d]pyrimidin-4(3H)-one:

6-(3-Benzyloxypropyl)-3-[2-(2,4-difluorophenyl)-2-hydroxy-3-[1,2,4]triazol-1-ylpropyl]-thieno[2,3-d]pyrimidin-4(3H)-one:

3-[2-(2,4-Difluorophenyl)-2-hydroxy-3-[1,2,4]triazol-1-yl-propyl]-6-(n-hexyl)-thieno[2,3-d]pyrimidin-4(3H)-one:

3-[2-(2,4-Difluorophenyl)-2-hydroxy-3-[1,2,4]triazol-1-yl-propyl]-6-n-pentylthieno[2,3-d]pyrimidin-4(3H)-one:

5-n-Butyl-3-[2-(2,4-difluorophenyl)-2-hydroxy-3-[1,2,4]triazol-1-yl-propyl]-6-n-propyl-thieno[2,3-d]pyrimidin-4(3H)-one:

3-[2-(2,4-Difluorophenyl)-2-hydroxy-3-[1,2,4]triazol-1-yl-propyl]-6-n-heptylthieno[2,3-d]pyrimidin-4(3H)-one:

3-[2-(2,4-Difluorophenyl)-2-hydroxy-3-[1,2,4]triazol-1-yl-propyl]-3,5,6,7-tetrahydrocyelopenta[4,5]thieno[2,3-d]pyrimidin-4(3H)-one:

3-[2-(2,4-Difluorophenyl)-2-hydroxy-3-[1,2,4]triazol-1-yl-propyl]-6-methyl-5-n-pentyl-thieno[2,3-d]pyrimidin-4(3H)-one:

3-[2-(2,4-Difluorophenyl)-2-hydroxy-3-[1,2,4]triazol-1-yl-propyl]-5,6,7,8-tetrahydrobenzothieno[2,3-d]pyrimidin-4(3H)-one:

3-[2-(2,4-Difluorophenyl)-2-hydroxy-3-[1,2,4]triazol-1-yl-propyl]-6-n-hexyl-5-methyl-thieno[2,3-d]pyrimidin-4(3H)-one:

3-[2-(2,4-Difluorophenyl)-2-hydroxy-3-[1,2,4]triazol-1-yl-propyl]-5-methyl-6-n-pentyl-thieno[2,3-d]pyrimidin-4(3H)-one:

6-(7-Acetoxyheptyl)-3-[2-(2,4-difluorophenyl)-2-hydroxy-3-[1,2,4]triazol-1-yl-propyl]-thieno[2,3-d]pyrimidin-4(3H)-one:

3-[2-(2,4-Difluorophenyl)-2-hydroxy-3-[1,2,4]triazol-1-yl-propyl]-6-(7-hydroxyheptyl)-thieno[2,3-d]pyrimidin-4(3H)-one:

3-[2-(2,4-Difluorophenyl)-2-hydroxy-3-[1,2,4]triazol-1-yl-propyl]-5(2-phenylethyl)-thieno[2,3-d]pyrimidin-4(3H)-one:

6-Benzyl-3-[2-(2,4-difluorophenyl)-2-hydroxy-3-[1,2,4]triazol-1-yl-propyl]-5-methyl-thieno[2,3-d]pyrimidin-4(3H)-one:

6-n-Decyl-3-[2-(2,4-difluorophenyl)-2-hydroxy-3-[1,2,4]triazol-1-yl-propyl]-thieno[2,3-d]pyrimidin-4(3H)-one:

3-[2-(2,4-Difluorophenyl)-2-hydroxy-3-[1,2,4]triazol-1-yl-propyl]-6-n-nonylthieno[2,3-d]pyrimidin-4(3H)-one:

3-[2-(2,4-Difluorophenyl)-2-hydroxy-3-[1,2,4]triazol-1-yl-propyl]-6-(n-propyl)-thieno[2,3-d]pyrimidin-4(3H)-one:

3-[2-(2,4-Difluorophenyl)-2-hydroxy-3-[1,2,4]triazol-1-yl-propyl]-3,5,6,7,8,9,10,11,12,13,14-undecahydrocyclododeca[4,5]thieno[2,3-d]pyrimidin-4(3H)-one:

3-[2-(2,4-Difluorophenyl)-2-hydroxy-3-[1,2,4]-triazol-1-yl-propyl]-5-methyl-6-n-octyl-thieno[2,3-d]pyrimidin-4(3H)-one:

3,-[2-(2,4-Difluorophenyl)-2-hydroxy-3-[1,2,4]triazol-1-yl-propyl]-6-n-butyl-5-methyl-thieno[2,3-d]pyrimidin-4(3H)-one:

3-[2-(2,4-Difluorophenyl)-2-hydroxy-3-[1,2,4]triazol-yl-propyl]-6-ethylthieno[2,3-d]pyrimidin-4(3H)-one:

3-[2-(2,4-Difluorophenyl)-2-hydroxy-3-[1,2,4]triazol-1-yl-propyl]-6-(4-hydroxybutyl)-thieno[2,3-d]pyrimidin-4(3H)-one:

3-[2-(2,4-Difluorophenyl)-2-hydroxy-3-[1,2,4]triazol-1-yl-propyl]-6-(4-N-Bocaminoacetyloxybutyl)-thieno[2,3-d]pyrimidin-4(3H)-one:

3-[2-(2,4-Difluorophenyl)-2-hydroxy-3-[1,2,4]triazol-1-yl-propyl]-6-(4-aminoacetyloxybutyl)-thieno[2,3-d]pyrimidin-4(3H)-one:

3-[2-(2,4-Difluorophenyl)-2-hydroxy-3-[1,2,4]triazol-1-yl-propyl]-6-(3-acetoxypropyl)-thieno[2,3-d]pyrimidin-4(3H)-one:

3-[2-(2,4-Difluorophenyl)-2-hydroxy-3-[1,2,4]triazol-1-yl-propyl]-6-(3-hydroxypropyl)-thieno[2,3-d]pyrimidin-4(3H)-one: or 3-[2-(2,4-Difluorophenyl)-2-hydroxy-3-[1,2,4]triazol-1-yl-propyl]-6-methylthieno[2,3-d]pyrimidin-4(3H)-one.

4. A pharmaceutical composition comprising an antifungal compound of formula (1) according to claim 1, with at least one pharmaceutical excipient.

5. A pharmaceutical composition comprising an antifungal compound prepared according to the process of claim 2, with at least one pharmaceutical excipient.

6. A pharmaceutical composition comprising a compound according to claim 3, with at least one pharmaceutical excipient.

7. A method for treating or preventing a fungal infection in a subject, which method comprises administering an effective amount of a compound according to claim 1, with pharmaceutical excipients.

8. A method for treating or preventing a fungal infection in a subject, which method comprises administering an effective amount of an antifungal compound prepared according to the process of claim 2, with pharmaceutical excipients.

9. A method for treating or preventing a fungal infection in a subject, which method comprises administering an effective amount of a compound according to claim 3, with pharmaceutical excipients.

10. A compound according to claim 1, wherein R3 and R4 together form an alkylene chain of formula —$(CH_2)_n$—, n being between 3 and 10.

11. A process according to claim 2, wherein R3 and R4 together form an alkylene chain of formula —$(CH_2)_n$—, n being between 3 and 10.

* * * * *